US007179614B2

(12) United States Patent
Margolskee et al.

(10) Patent No.: US 7,179,614 B2
(45) Date of Patent: Feb. 20, 2007

(54) SCREENING METHODS TO IDENTIFY COMPOUNDS THAT MODULATE TYPE I PHOSPHODIESTERASE (PDE) ACTIVITY

(75) Inventors: Robert Margolskee, Upper Montclair, NJ (US); Joseph Beavo, Seattle, WA (US)

(73) Assignees: Mount Sinai School of Medicine, New York, NY (US); University of Washington, Seattle, WA (US)

( * ) Notice: Subject to any disclaimer, the term of this patent is extended or adjusted under 35 U.S.C. 154(b) by 400 days.

(21) Appl. No.: 10/380,393

(22) PCT Filed: Sep. 14, 2001

(86) PCT No.: PCT/US01/28663

§ 371 (c)(1),
(2), (4) Date: Mar. 12, 2003

(87) PCT Pub. No.: WO02/22649

PCT Pub. Date: Mar. 21, 2002

(65) Prior Publication Data

US 2004/0063148 A1    Apr. 1, 2004

Related U.S. Application Data

(60) Provisional application No. 60/232,552, filed on Sep. 14, 2000.

(51) Int. Cl.
*C12Q 1/44* (2006.01)
(52) U.S. Cl. ........................................................ 435/19
(58) Field of Classification Search .................. 435/4, 435/19, 195, 196
See application file for complete search history.

(56) References Cited

U.S. PATENT DOCUMENTS

| | | | |
|---|---|---|---|
| 5,034,506 A | 7/1991 | Summerton et al. | |
| 5,168,062 A | 12/1992 | Stinski | |
| 5,385,839 A | 1/1995 | Stinski | |
| 5,389,527 A | 2/1995 | Beavo et al. | |
| 5,580,771 A * | 12/1996 | Beavo et al. | 435/199 |
| 5,602,019 A | 2/1997 | Beavo et al. | |
| 5,637,684 A | 6/1997 | Cook et al. | |
| 5,652,131 A | 7/1997 | Beavo et al. | |
| 5,677,437 A | 10/1997 | Teng et al. | |
| 5,702,936 A | 12/1997 | Beavo et al. | |
| 5,776,752 A | 7/1998 | Beavo et al. | |
| 5,780,607 A | 7/1998 | Goodnow, Jr. et al. | |
| 5,783,682 A | 7/1998 | Cook et al. | |
| 5,789,553 A | 8/1998 | Beavo et al. | |
| 5,792,844 A | 8/1998 | Sanghvi et al. | |
| 5,811,234 A | 9/1998 | Roninson et al. | |
| 5,814,500 A | 9/1998 | Dietz | |
| 5,817,759 A * | 10/1998 | Margolskee | 530/350 |
| 6,001,553 A * | 12/1999 | Broach et al. | 435/4 |
| 6,008,000 A | 12/1999 | Margolskee | |
| 6,015,677 A | 1/2000 | Beavo et al. | |
| 6,037,119 A | 3/2000 | Beavo et al. | |
| 6,852,906 B2 * | 2/2005 | Craig et al. | 800/3 |
| 2003/0143588 A1 * | 7/2003 | Thornton et al. | 435/6 |

FOREIGN PATENT DOCUMENTS

| | | | |
|---|---|---|---|
| CA | 2135253 | * | 5/1996 |
| EP | 0 372 707 | | 6/1990 |
| WO | WO 92/05263 | | 4/1992 |
| WO | WO 94/21807 | | 9/1994 |
| WO | WO 95/28494 | | 10/1995 |
| WO | WO 00/27861 | * | 5/2000 |
| WO | WO00/27861 | | 5/2000 |

OTHER PUBLICATIONS

Ho, A. et al. Ca+2 Calmodulin Modulation of GTP Binding Protein. Biochemical Archives 14(4)227-239, Nov. 1998.*
Avila et al., Coupling of bitter receptor phosphodiesterase through transducin receptor cells, Nature, vol. 376, 80-85 (1995).
Sonnenburg et al., Ident, Quant, and Cell Local of PDEI Calm.Stim Cyc Nuc PE, Methods: A Comparison to Methods in Enzymology14,3-19 (1998).
Kakkar et al., Calm.-dep. Nuc. PDE 1, Cell Mol.Sci. 55 1164-1186 (1999).
Weishaar et al.,A New Generation of Phosphodiesterase Inhibitors, J.Med.Chem.,V. 28, No. 5, 537-545 (1985).
Adler et al., "A Novel Family of Mammalian Taste Receptors," Cell 100(6):693-702 (2000).
"Animal Cell Culture: A Practical Approach," R.I. Freshney, ed., IRL Press, Oxford, Washington D.C. (1986) (Table of Contents only).

(Continued)

*Primary Examiner*—Ralph Gitomer
(74) *Attorney, Agent, or Firm*—Nixon Peabody LLP

(57) ABSTRACT

The present invention relates to novel methods of signal transduction in cells. In particular, the invention relates to signal transduction via a class of enzymes known as phosphodiesterase enzymes or PDEs. The invention also relates to a class of signaling molecules known as G-coupled protein receptors (GCPRs) and G-proteins. The invention provides novel methods to screen for and identify G-proteins and other compounds which modulate signaling by these two classes of proteins. In particular, the relates to novel assays which identify compounds that modulate (e.g., enhance or inhibit) binding between a PDE polypeptide and an effector activation domain of a G-protein.

15 Claims, 8 Drawing Sheets

OTHER PUBLICATIONS

Figure 1B:
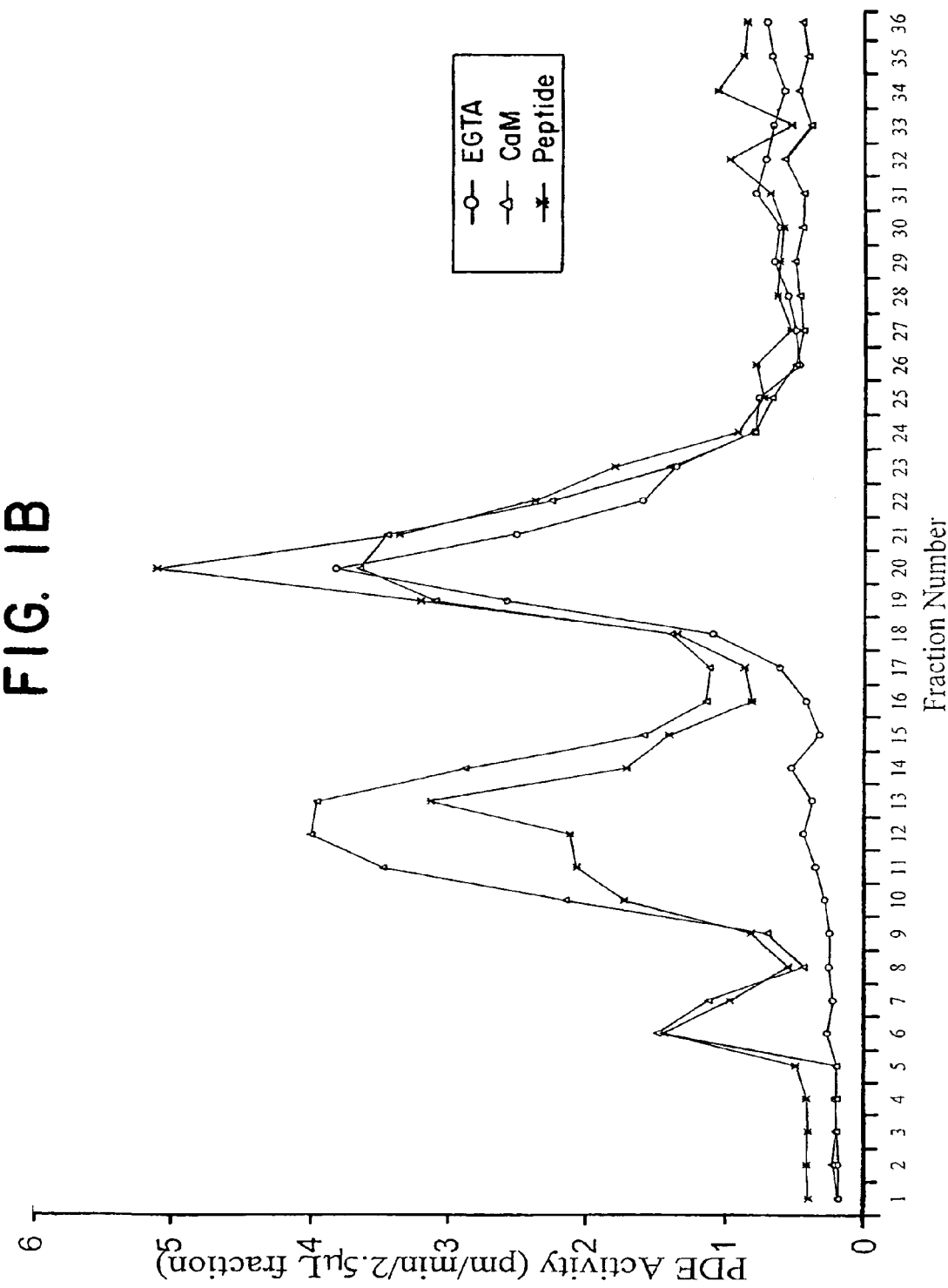

Ausubel et al., "Current Protocols in Molecular Biology," Green Publishing Associates, Inc. and John Wiley and Sons, Inc., New York (1994) (Table of Contents only).

Bakre et al., "Expression and Regulation of the cGMP-Binding, cGMP-Specific Phosphodiesterase (PDE5) in Human Colonic Epithelial Cells: Role in the Induction of Cellular Refractoriness to the Heat-Stable Enterotoxin Peptide," *J. Cellular Biochem.* 77(1):159-167 (2000).

Beavo, J., "Multiple Phosphodiesterase Isozymes: Background, Nomenclature and Implications," in *Cyclic Nucleotide Phosphodiesterases: Structure, Regulation and Drug Action*, Beavo and Houslay, Eds., John Wiley & Sons, New York, pp. 3-15 (1990).

Beavo, J.A., "Multiple Isozymes of Cyclic Nucleotide Phosphodiesterase," *Adv. in Second Mess. and Phosphoprotein Res.* 22:1-38 (1988).

Benoist & Chambon, "*In vivo* Sequence Requirements of the SV40 Early Promoter Region," *Nature* 290(5801):304-310 (1981).

Birnbaumer, L., "G Proteins in Signal Transduction," *Annu. Rev. Pharmacol. Toxicol.* 30:675-705 (1990).

Brand et al., "Inhibition by Amiloride of Chorda Tympani Responses Evoked by Monovalent Salts," *Brain Research* 334(2):207-214 (1985).

Brinster et al., "Regulation of Metallothionein-Thymidine Kinase Fusion Plasmids Injected Into Mouse Eggs," *Nature* 296(5852):39-42 (1982).

Chandrashekar et al., "T2Rs Function as Bitter Taste Receptors," *Cell* 100:703-711 (2000).

Chaudhari et al., "A Metabotropic Glutamate Receptor Variant Functions as a Taste Receptor," *Nat. Neurosci.* 3(2):113-119 (2000).

Chaudhari & Roper, "Molecular and Physiological Evidence for Glutamate (*Umami*) Taste Transduction via a G Protein-Coupled Receptor," *Annals New York Academy of Sciences* 855:398-406 (1998).

De Boer et al., "The *tac* Promoter: A Functional Hybrid Derived from the *trp* and *lac* Promoters," *Proc. Natl. Acad. Sci. USA* 80:21-25 (1983).

"DNA Cloning: A Practical Approach," Vols. I and II, D.M. Glover ed., IRL Press, Oxford, Washington D.C. (1985) (Table of Contents only).

GenBank Accession No. AAA96961 (Apr. 10, 1996).
GenBank Accession No. AAB50017 (Mar. 21, 1997).
GenBank Accession No. AAB50018 (Mar. 21, 1997).
GenBank Accession No. AAC50436 (Jan. 9, 1996).
GenBank Accession No. AAC50437 (Jan. 9, 1996).
GenBank Accession No. NP_005010 (May 14, 1999).
GenBank Accession No. NP_005011 (May 14, 1999).
GenBank Accession No. P14100 (May 30, 2000).
GenBank Accession No. P54750 (May 30, 2000).
GenBank Accession No. Q14123 (Dec. 15, 1998).

Gilbert & Villa-Komaroff, "Useful Proteins from Recombinant Bacteria," *Scientific America* 242:74-94 (1980).

Gilbertson et al., "Proton Currents Through Amiloride-Sensitive Na Channels in Hamster Taste Cells: Role in Acid Transduction," *J. Gen. Physiol.* 100(5):803-824 (1992).

Gilbertson et al., "The Molecular Physiology of Taste Transduction," *Curr. Opin. Neurobiol.* 10:519-527 (2000).

Greenberg et al., "Enzymatic Regulation of the Concentration of Cyclic GMP in Mouse Brain," *Neuropharmacol.* 17:737-745 (1978).

Hansen & Beavo, "Differential Recognition of Calmodulin-Enzyme Complexes by a Conformation-Specific Anti-Calmodulin Monoclonal Antibody," *J. Biol. Chem.* 261(31)14636-14645 (1986).

Hansen & Beavo, "Purification of Two Calcium/Calmodulin-Dependent Forms of Cyclic Nucleotide Phosphodiesterase by Using Conformation-Specific Monoclonal Antibody Chromatography," *Proc. Natl. Acad. Sci. USA* 79:2788-2792 (1982).

Heck et al., "Salt Taste Transduction Occurs Through an Amiloride-Sensitive Sodium Transport Pathway," *Science* 223(4634):403-405 (1984).

Houghten et al., "Generation and Use of Synthetic Peptide Combinatorial Libraries for Basic Research and Drug Discovery," *Nature* 354(6348):84-86 (1991).

Huang et al., "Gγ13 Colocalizes with Gustducin in Taste Receptor Cells and Mediates $IP_3$ Responses to Bitter Denatonium," *Nature Neuroscience* 2(12):1055-1062 (1999).

"Immobilised Cells and Enzymes: A Practical Approach," J. Woodward ed., IRL Press, Oxford, Washington D.C. (1985) (Table of Contents only).

Juilfs et al., "A Subset of Olfactory Neurons That Selectively Express cGMP-Stimulated Phosphodiesterase (PDE2) and Guanylyl Cyclase-D Define a Unique Olfactory Signal Transduction Pathway," *Proc. Natl. Acad. Sci. USA* 94:3388-3395 (1997).

Kaplitt et al., "Expression of a Functional Foreign Gene in Adult Mammalian Brain Following *in Vivo* Transfer via a Herpes Simplex Virus Type 1 Defective Viral Vector," *Molec. Cell. Neurosci.* 2(4):320-330 (1991).

Kincaid et al., "Differential Localization of Calmodulin-Dependent Enzymes in Rat Brain: Evidence for Selective Expression of Cyclic Nucleotide Phosphodiesterase in Specific Neurons," *Proc. Natl. Acad. Sci. USA* 84:1118-1122 (1987).

Kinnamon et al., "Apical Localization of $K^+$ Channels in Taste Cells Provides the Basis for Sour Taste Transduction," *Proc. Natl. Acad. Sci. USA* 85(18):7023-7027 (1988).

Kinnamon & Cummings, "Chemosensory Transduction Mechanisms in Taste," *Annu. Rev. Physiol.* 54:715-731 (1992).

Kolesnikov & Margolskee, "A Cyclic-Nucleotide-Suppressible Conductance Activated by Transducin in Taste Cells," *Nature* 376(6535):85-88 (1995).

Lam et al., "A New Type of Synthetic Peptide Library for Identifying Ligand-Binding Activity," *Nature* 354(6348):82-84 (1991).

LaPorte et al., "Cross-Linking of Iodine-125-Labeled, Calcium-Dependent Regulatory Protein to the $Ca^{2+}$-Sensitive Phosphodiesterase Purified from Bovine Heart," *Biochemistry* 18(13):2820-2825 (1979).

La Salle et al., "An Adenovirus Vector for Gene Transfer into Neurons and Glia in the Brain," *Science* 259(5097):988-990 (1993).

Lebkowski et al., "Adeno-Associated Virus: A Vector System for Efficient Introduction and Integration of DNA into a Variety of Mammalian Cell Types," *Mol. Cell. Biol.* 8(10):3988-3996 (1988).

Lerea et al., "Identification of Specific Transducin α Subunits in Retinal Rod and Cone Photoreceptors," *Science* 234:77-80 (1986).

Lindemann, B., "Chemoreception: Tasting the Sweet and the Bitter," *Curr. Biol.* 6(10):1234-1237 (1996).

Lindemann, B., "Receptors and Transduction in Taste," *Nature* 413:219-225 (2001).

Lindemann, B., "Taste Reception," *Physiol. Rev.* 76(3):719-766 (1996).

Liu et al., "Mechanism of Allosteric Regulation of the Rod cGMP Phosphodiesterase Activity by the Helical Domain of Transducin α Subunit," *Journal of Biological Chemistry* 273(51):34284-34292 (1998).

Manganiello et al., "Cyclic GMP-Stimulated Cyclic Nucleotide Phosphodiesterases," in *Cyclic Nucleotide Phosphodiesterases: Structure, Regulation and Drug Action*, Beavo and Houslay, Eds., John Wiley & Sons, New York, pp. 62-85 (1990).

Maxam & Gilbert, "A New Method for Sequencing DNA," *Proc. Natl. Acad. Sci. USA* 74(2):560-564 (1977).

McLaughlin et al., "Gustducin is a Taste-Cell-Specific G Protein Closely Related to the Transducins," *Nature* 357(18):563-569 (1992).

Miller & Rosman, "Improved Retroviral Vectors for Gene Transfer and Expression," *BioTechniques* 7(9):980-990 (1992).

Ming et al., "Characterization and Solubilization of Bitter-Responsive Receptors That Couple to Gustducin," *Proc. Natl. Acad. Sci. USA* 95:8933-8938 (1998).

Misaka et al., "Taste Buds Have A Cyclic Nucleotide-Activated Channel, CNGgust," *J. Biol. Chem.* 272(36):22623-22629 (1997).

Nielsen et al., "Sequence-Selective Recognition of DNA by Strand Displacement with a Thymine-Substituted Polyamide," *Science* 254(5037):1497-1500 (1991).

"Nucleic Acid Hybridisation: A Practical Approach," B.D. Hames & S.J. Higgins eds., IRL Press, Oxford, Washington D.C. (1985) (Table of Contents only).

"Oligonucleotide Synthesis: A Practical Approach," M.J. Gait ed., IRL Press, Oxford, Washington D.C. (1984) (Table of Contents only).

Perbal, B., "A Practical Guide to Molecular Cloning," John Wiley and Sons, Inc., New York (1984) (Table of Contents only).

Reeck et al., "'Homology' in Proteins and Nucleic Acids: A Terminology Muddle and a Way Out of It," *Cell* 50(5):667 (1987).

Roper, S.D., "The Cell Biology of Vertebrate Taste Receptors," *Ann. Rev. Neurosci.* 12:329-353 (1989).

Rössler et al., "Identification of a Phospholipase C β Subtype in Rat Taste Cells," *European Journal Of Cell Biology* 77:253-261 (1998).

Rybalkin et al., "Calmodulin-Stimulated Cyclic Nucleotide Phosphodiesterase (PDE1C) Is Induced in Human Arterial Smooth Muscle Cells of the Synthetic, Proliferative Phenotype," *J. Clin. Invest.* 100(10):2611-2621 (1997).

Saiki et al., "Primer-Directed Enzymatic Amplification of DNA with a Thermostable DNA Polymerase," *Science* 239:487-491 (1988).

Sambrook et al., "Molecular Cloning," 2nd Ed. Cold Spring Harbor Laboratory Press (1989) (Table of Contents only).

Samulski et al., "A Recombinant Plasmid from Which an Infectious Adeno-Associated Virus Genome Can Be Excised In Vitro and Its Use To Study Viral Replication," *J. Virol.* 61(10):3096-3101 (1987).

Samulski et al., "Helper-Free Stocks of Recombinant Adeno-Associated Viruses: Normal Integration Does Not Require Viral Gene Expression," *J. Virol.* 63(9):3822-3828 (1989).

Sanger et al., "DNA Sequencing with Chain-Terminating Inhibitors," *Proc. Natl. Acad. Sci. USA* 74(12):5463-5467 (1977).

Sharma & Wang, "Purification and Characterization of Bovine Lung Calmodulin-Dependent Cyclic Nucleotide Phosphodiesterase," *J. Biol. Chem.* 261(30):14160-14166 (1986).

Simon et al., "Diversity of G Proteins in Signal Transduction," *Science* 252:802-808 (1991).

Smith & Johnson, "Single-Step Purification of Polypeptides Expressed in *Escherichia coli* as Fusions with Glutathione S-Transferase," *Gene* 67:31-40 (1988).

Snyder et al., "Isolation, Expression and Analysis of Splice Variants of a Human $Ca^{2+}$/Calmodulin-Stimulated Phosphodiesterase (PDE1A)," *Cell. Signal.* 11(7):535-544 (1999).

Songyang et al., "SH2 Domains Recognize Specific Phosphopeptide Sequences," *Cell* 72:767-778 (1993).

Spickofsky et al., "Biochemical Analysis of the Transducin-Phosphodiesterase Interaction," *Nat. Struct. Biol.* 1(11):771-781 (1994).

Stewart et al., "New Perspectives in Gustatory Physiology: Transduction, Development, and Plasticity," *Am. J. Physiol.* 272(1):C1-C26 (1997).

Stone et al., "Virus-Mediated Transfer of Foreign DNA into Taste Receptor Cells," *Chem. Senses* 27:779-787 (2002).

Stratford-Perricaudet et al., "Widespread Long-Term Gene Transfer to Mouse Skeletal Muscles and Heart," *J. Clin. Invest.* 90:626-630 (1992).

Striem et al., "Sweet Tastants Stimulate Adenylate Cyclase Coupled to GTP-Binding Protein in Rat Tongue Membranes," *Biochem. J.* 260:121-126 (1989).

Villa-Komaroff et al., "A Bacterial Clone Synthesizing Proinsulin," *Proc. Natl. Acad. Sci. USA* 75(8):3727-3731 (1978).

Wagner et al., "Nucleotide Sequence of the Thymidine Kinase Gene of Herpes Simplex Virus Type 1," *Proc. Natl. Acad. Sci. USA* 78(3):1441-1445 (1981).

Wang et al., "Calmodulin-Stimulated Cyclic Nucleotide Phosphodiesterases," in *Cyclic Nucleotide Phosphodiesterases: Structure, Regulation and Drug Action,* Beavo & Housley, Eds., John Wiley & Sons, New York, pp. 19-59 (1990).

Wong et al., "Transduction of Bitter and Sweet Taste by Gustducin," *Nature* 381(6585):796-800 (1996).

Yamamoto et al., "Identification of a Functional Promoter in the Long Terminal Repeat of Rous Sarcoma Virus," *Cell* 22(1):787-797 (1980).

Yan et al., "The Calmodulin-Dependent Phosphodiesterase Gene *PDE1C* Encodes Several Functionally Diffferent Splice Variants in a Tissue-Specific Manner," *J. Biol. Chem.* 271(41):25699-25706 (1996).

Charbonneau et al., "Evidence for Domain Organization within the 61-kDa Calmodulin-dependent Cyclic Nucleotide Phosphodiesterase from Bovine Brain," *Biochem.* 30(32):7931-7940 (1991).

Charbonneau et al., "Identification of a Conserved Domain among Cyclic Nucleotide Phosphodiesterases from Diverse Species," *PNAS USA* 83(24):9308-9312 (1986).

Spence et al., "Receptor-mediated Stimulation of Lipid Signalling Pathways in CHO Cells Elicits the Rapid Transient Induction of the PDE1B Isoform of $Ca^{2+}$/Calmodulin-stimulated cAMP Phosphodiesterase," *Biochem. J.* 321:157-163 (1997).

Zhao et al., "Recent Advances in the Study of $Ca^{2+}$/CaM-activated Phosphodiesterases: Expression and Physiological Functions," *Adv. Second Messenger Phosphoprotein Res.* 31:237-251 (1997).

* cited by examiner

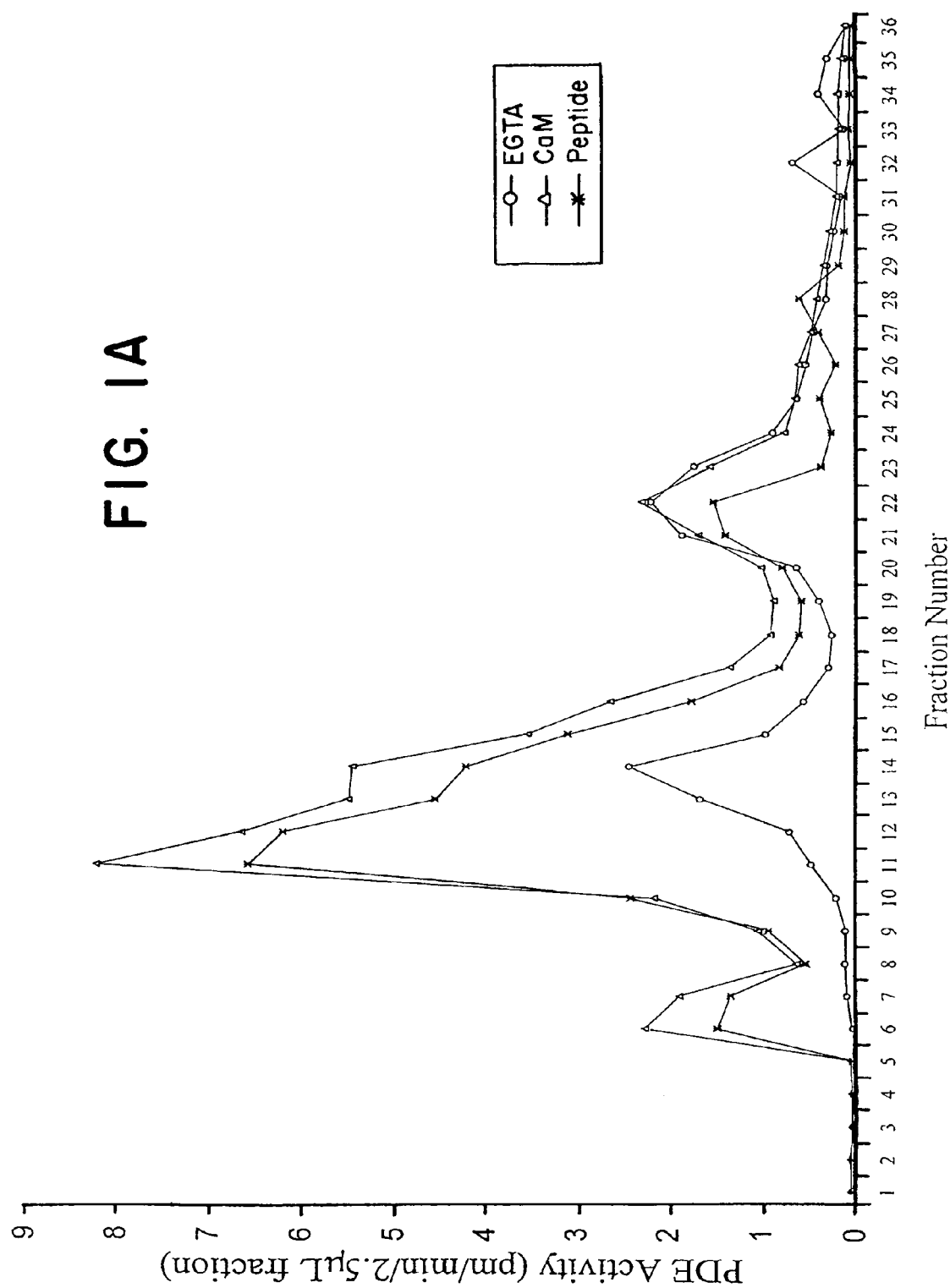

FIG. 6

```
  1  mgagasaeek hsrelekklk edaekdartv klllgages gkstivkqmk iihgdgysle
 61  eclefiaiiy gntlqsilai vramttlniq ygdsarqdda rklmhmadti eegtmpkems
121  diiqrlwkds gigacfdras eyqlndsagy ylsdlerlvt pgyvpteqdv lrsrvkttgi
181  ietqfsfkdl nfrmfdvggq rserkkwihc fegvtciifi aalsaydmvl veddevnrmh
241  eslhlfnsic nhryfattsi viflnkkdvf sekikkahls icfpdyngpn tyedagnyik
301  vqflelnmrr dvkeiyshmt catdtqnvkf vfdavtdiii kenlkdcglf
```

US 7,179,614 B2

SCREENING METHODS TO IDENTIFY COMPOUNDS THAT MODULATE TYPE I PHOSPHODIESTERASE (PDE) ACTIVITY

This application is a 371 of PCT/US01/28663 filed Sep. 14, 2001 which claims benefit of Provisional Application 60/232,552 filed Sep. 14, 2000.

This invention was made with Government support under Grant No. DK-21723 awarded by the National Institutes of Health, under Grant No. IBN-9816782 awarded by the National Science Foundation, and under Grant No. 5 R01 DC03055 awarded by the National Institute on Deafness and Other Communication Disorders. The United States Government may have certain rights to this invention pursuant to these grants.

Numerous references, including patents, patent applications and various publications, are cited and discussed in the description of this invention. The citation and/or discussion of such references is provided merely to clarify the description of the present invention and is not an admission that any such references is "prior art" to the invention described herein. All references cited and discussed in this specification are incorporated herein by reference in their entirety and to the same extent as if each reference was individually incorporated by reference.

1. FIELD OF THE INVENTION

The present invention relates to novel methods of signal transduction in cells. In particular, the invention relates to signal transduction via a class of enzymes known as phosphodiesterase enzymes or PDEs. The invention also relates to a class of signaling molecules known as G-coupled protein receptors (GCPRs) and G-proteins. The invention provides novel methods to screen for and identify G-proteins and other compounds which modulate signaling by these two classes of proteins. In particular, the relates to novel assays which identify compounds that modulate (e.g., enhance or inhibit) binding between a PDE polypeptide and an effector activation domain of a G-protein.

2. BACKGROUND OF THE INVENTION

Cyclic nucleotides are known to mediate a wide variety of cellular responses to biological stimuli. The cyclic nucleotide phosphodiesterases (PDEs) are proteins which catalyze hydrolysis of 3', 5'-cyclic nucleotides, such as cyclic adenosine monophosphate (cAMP) and cyclic guanosine monophosphate (cGMP), to their corresponding 5'-nucleotide monophosphates. These enzymes are therefore important in control of cellular concentration of cyclic nucleotides and have a central role in a variety of intracellular signaling events, including signaling by such mechanisms and extracellular hormones, neurotransmitters and the like.

At least five distinct families of PDEs have been identified (for a review, see Beavo, *Adv. in Second Mess. and Prot. Phosph. Res.* 1988, 22:1–38; see also, Beavo, "Multiple Phosphodiesterase Isozymes: Background, Nomenclature and Implications", pp. 3–15 in *Cyclic Nucleotide Phosphodiesterases: Structure, Regulation and Drug Action* 1990, Beavo & Houslay, Eds., John Wiley & Sons, New York; Wang et al., "Calmodulin-Stimulated Cyclic Nucleotide Phosphodiesterases", pp. 19–59 in *Cyclic Nucleotide Phosphodiesterases: Structure, Regulation and Drug Action*, supra; and Manganiello et al., "Cyclic GMP-Stimulated Cyclic Nucleotide Phosphodiesterases", pp. 62–85 in *Cyclic Nucleotide Phosphodiesterases: Structure, Regulation and Drug Action*, supra). These five families include: Type I or calmodulin (CaM)-stimultated PDEs; Type II or cGMP-stimulated PDEs; Type III or cGMP-inhibited PDEs; Type IV or cAMP-specific PDEs; and Type V or cGMP-specific PDEs. In addition, within each of the above-identified families there are multiple forms and isoforms (i.e., splice-variants) of closely related PDEs.

The CaM-stimulated PDEs are defined by their responsiveness to intracellular calcium levels, which leads to decreased intracellular concentrations of cAMP and/or cGMP. Indeed, increased levels of PDE activity may be observed in response to CaM in nearly every type of mammalian tissue, as well as in *Drosophila*, *Dictyostelium* and *trypanosomes*. Most cells therefore appear to contain at least a small amount of CaM-stimulated PDE activity. Highest levels of CaM-stimulated PDE activity have been observed in the brain and, in particular, in synaptic areas (see Greenberg et al., *Neuropharmacol.* 1978, 17:737–745; and Kincaid et al., *Proc. Natl. Acad. Sci. U.S.A.* 1987, 84:1118–1122). Several members of the CaM-PDE family have been described and are known in the art. See, for example, U.S. Pat. No. 6,015,677, issued Jan. 18, 2000 to Beavo et al.; see also, LaPorte et al., *Biochemistry* 1979, 18:2820–2825; Hansen et al., *Proc. Natl. Acad. Sci. U.S.A.* 1982, 79:2788–2792; Sharmaetal., *J. Biol. Chem.* 1986, 261:14160–14166; Hansen et al., *J. Biol. Chem.* 1986, 261:14636–14645; Snyder et al., *Cell Signal* 1999, 11:535–544. See also Kakkar et al., *Cell Mol. Life Sci.* 1999, 55:1164–1186; and Weishaar et al., *J. Med. Chem.* 1985, 28:537–545 for reviews.

Guanine nucleotide binding proteins (G-proteins) are also of particular interest to the background of the present invention. G-proteins are well known in the art (see, e.g., reviews by Birnbaumer, *Ann. Rev. Pharmacol Toxicol.* 1990, 30:675–705; and Simon et al., *Science* 1991, 252:802–808). Briefly, G-proteins are heterotrimeric proteins, each having an $\alpha$-, $\beta$- and $\gamma$-subunit, which also mediate signal transduction in a variety of different systems, including olfactory, visual, hormonal and neurotransmitter systems. G-proteins couple cell surface receptors to cellular effector enzymes, and thereby transduce an extracellular signal into an intracellular second messenger. The $\alpha$-subunit of a G-protein confers most of the specificity of interaction between its receptor and effectors in the signal transduction process, while $\beta$- and $\gamma$-subunits appear to be shared among different G-proteins. Although some G-proteins (for example, $G_s$ abd $G_i$) are ubiquitously expressed, others (for example transducin and gustucin) are known to be involved in sensory transduction and have been found only in specialized sensory cells (see, for example Lerea et al., *Science* 1986, 224:77–80; see also U.S. Pat. No. 6,008,000 issued Dec. 28, 1999 to Margolskee.

Some evidence has suggested that at least a certain G-protein may effect signal transduction by activating some, unidentified phosphodiesterase. In particular, Ruiz-Avila et al. (*Nature* 1995, 376:80–85) have demonstrated that a transducin-derived peptide which mimics the effects of an activated G-protein stimulates cGMP PDE activity in bovine taste lingual-tissues. However, no direct interaction between G-protein and any particular PDE has been observed.

Given, however, the wide variety of signal transduction responses in which both G-proteins and phosphodiesterases are involved and the numerous disorders associated with these different responses, there exist a need for methods to identify specific compounds that modulate signal transduction by PDEs, G-proteins or both.

3. SUMMARY OF THE INVENTION

In addition to methods and systems for identifying compounds that modulate CaM-PDE activation by G-proteins, the present invention provides a method of inhibiting a calmodulin (CaM)-stimulated phosphodiesterase (PDE). This method comprises contacting the PDE with a compound that inhibits activation of the PDE by a G-protein.

In another aspect, the invention provides a method for identifying a PDE activated by a G-protein. This method comprises detecting activation of a PDE contacted with a polypeptide. The polypeptide comprises a G-protein activation peptide from an α-domain of a G-protein.

4. BRIEF DESCRIPTION OF THE DRAWINGS

Figure 1C:
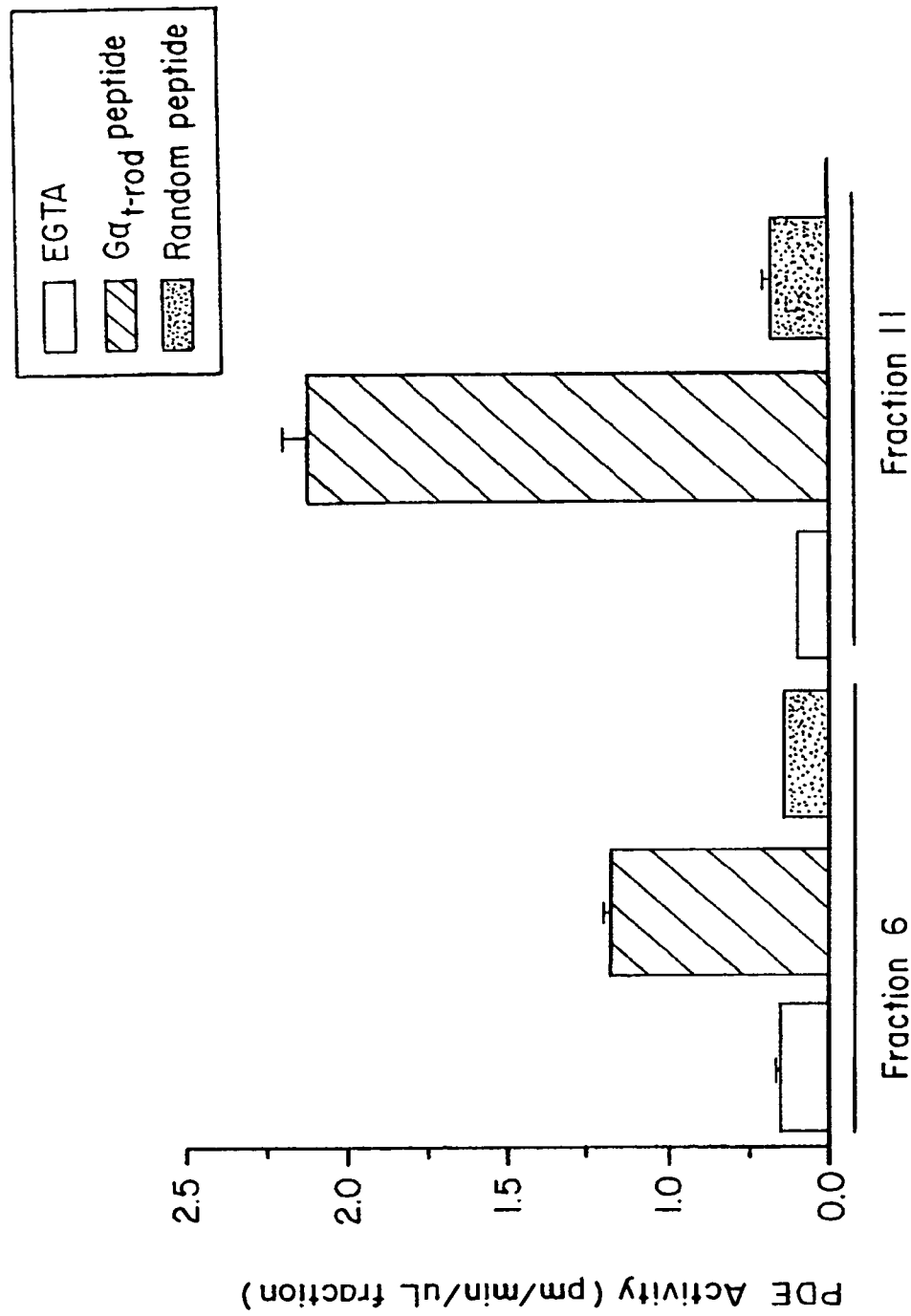

FIGS. 1A–1C. PDEs present in the cytoplasm of bovine circumvallate papillae were resolved by using anion exchange chromatography. Proteins were eluted from a DAEA column using a 0–1 M NaCl gradient. Assays of PDE activity in each fraction were performed as described in Section 6.1, infra using either 1 µM cGMP or 1 µM cAMP (FIGS. 1A and 1B, respectively) as substrates in the presence of either 1 mM EDTA (diamonds), 1 mM $CaCl_2$ and 4 µg/ml CaM (open squares) or 100 µM $G\alpha_{t\text{-}rod}$ peptide (asterix). FIG. 1C illustrates the specificiy to the peptide stimulated PDE activity from fractions shown in FIGS. 1A and 1B. Specifically, a "scrambled" peptide was synthesized which had the same amino acid residue composition as the $G\alpha_{t\text{-}rod}$ polypeptide but a randomized sequence. PDE assays were performed on fractions 6 and 11 from FIGS. 1A and 1B, in the absence of peptide (open bars), in the presence of 100 µM $G\alpha_{t\text{-}rod}$ polypeptide (hatched bars) or in the presence of 100 µM scrambled peptide (black bars) using 1 µM cGMP as the substrate.

Figure 2:
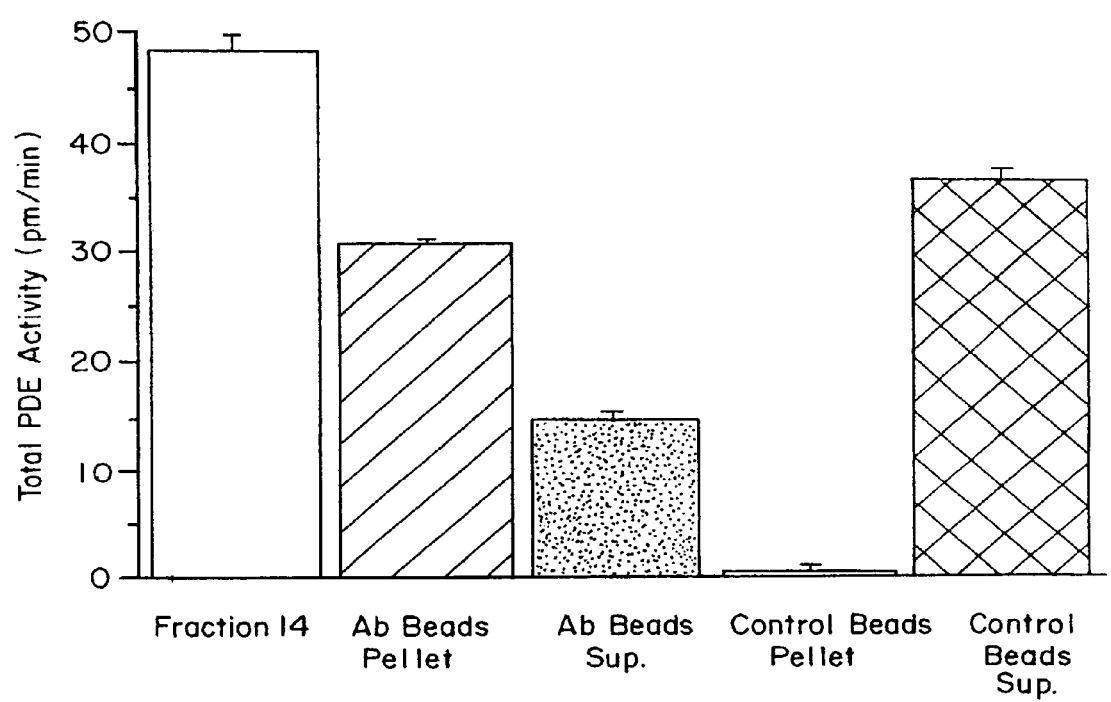

FIG. 2. Fraction 14 from the anion exchange chromatography fractions shown in FIGS. 1A and 1B was used to immunoprecipitate PDE5 using anti-PDE5 antibodies. Protein A beads were pre-incubated with ("Ab beads") or without ("control beads") antibody prior to immunoprecipitation. PDE activity was checked in the pellets precipitated with both Ab beads (hatched bar) and the control beads (labeled "Control Beads Pellet) in the presence of 1 mM EGTA using 1 µM cGMP as the substrate. PDE activity was also checked in the supernatant from experiments with the Ab beads (black bar) and the control beads (shaded bar).

Figure 3:
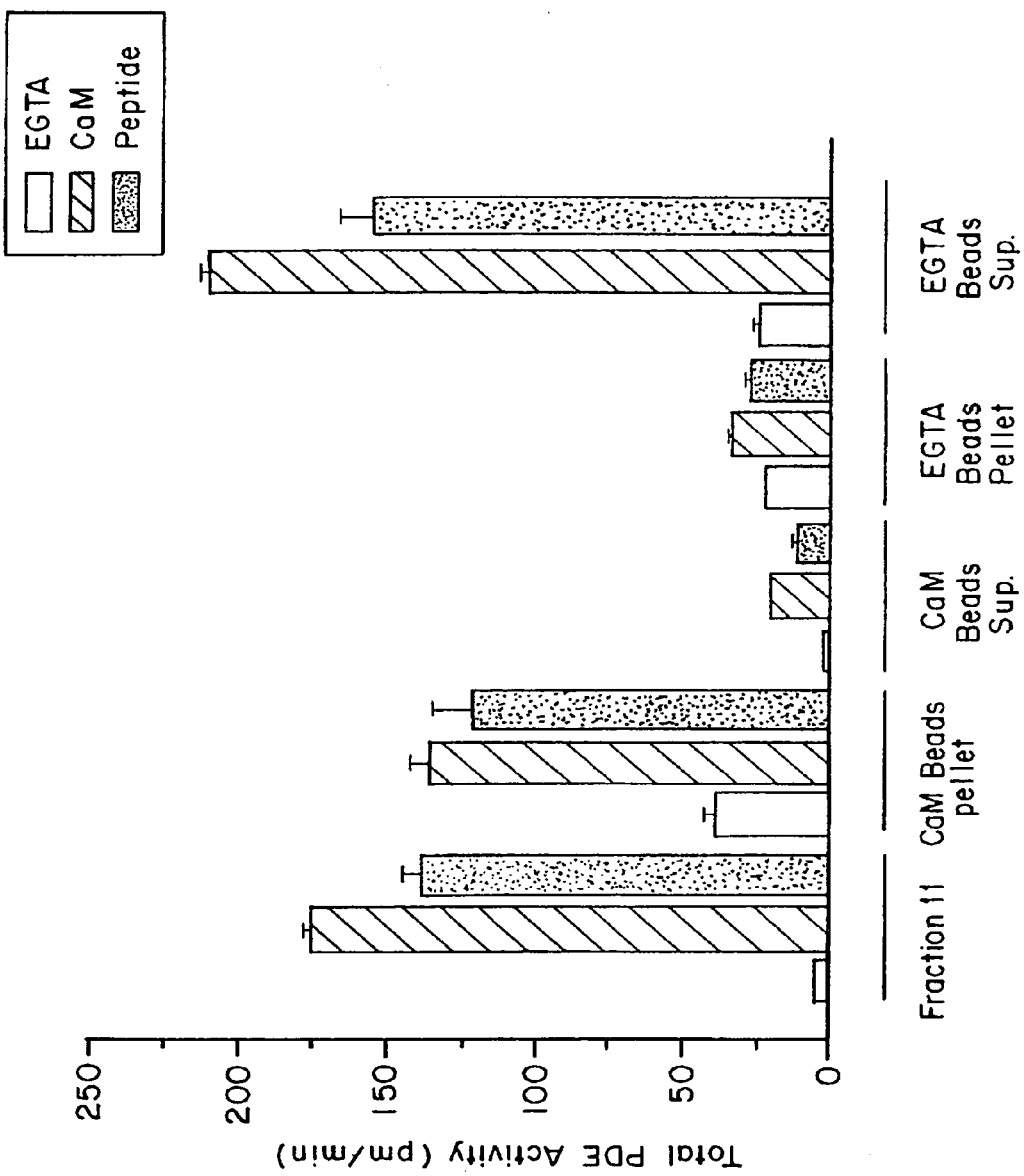

FIG. 3. CaM affinity chromatography was performed on fraction 11 (from the anion exchange fractions shown in FIGS. 1A and 1B) using CaM-Sepharose beads either in the presence of 2 mM $CaCl_2$ (CaM beads) or in the presence of 2 mM EGTA (EGTA beads). The beads (pellets) were checked for PDE activity using cGMP (1 µM) as the substrate, in the presence of 2 mM EGTA (open bars), 1 mM $CaCl_2$ and 4 µg/ml CaM (hatched bars), or 100 µM $G\alpha_{t\text{-}rod}$ peptide (filled bars). Excess $CaCl_2$ was supplied during the assay when the affinity interaction was performed in presence of EGTA. The supernatant and the washes showed very little or no phosphodiesterase activity (data not shown). All values are expressed as mean plus or minus standard error of mean of at least three independent experiments performed in triplicate.

Figure 4:
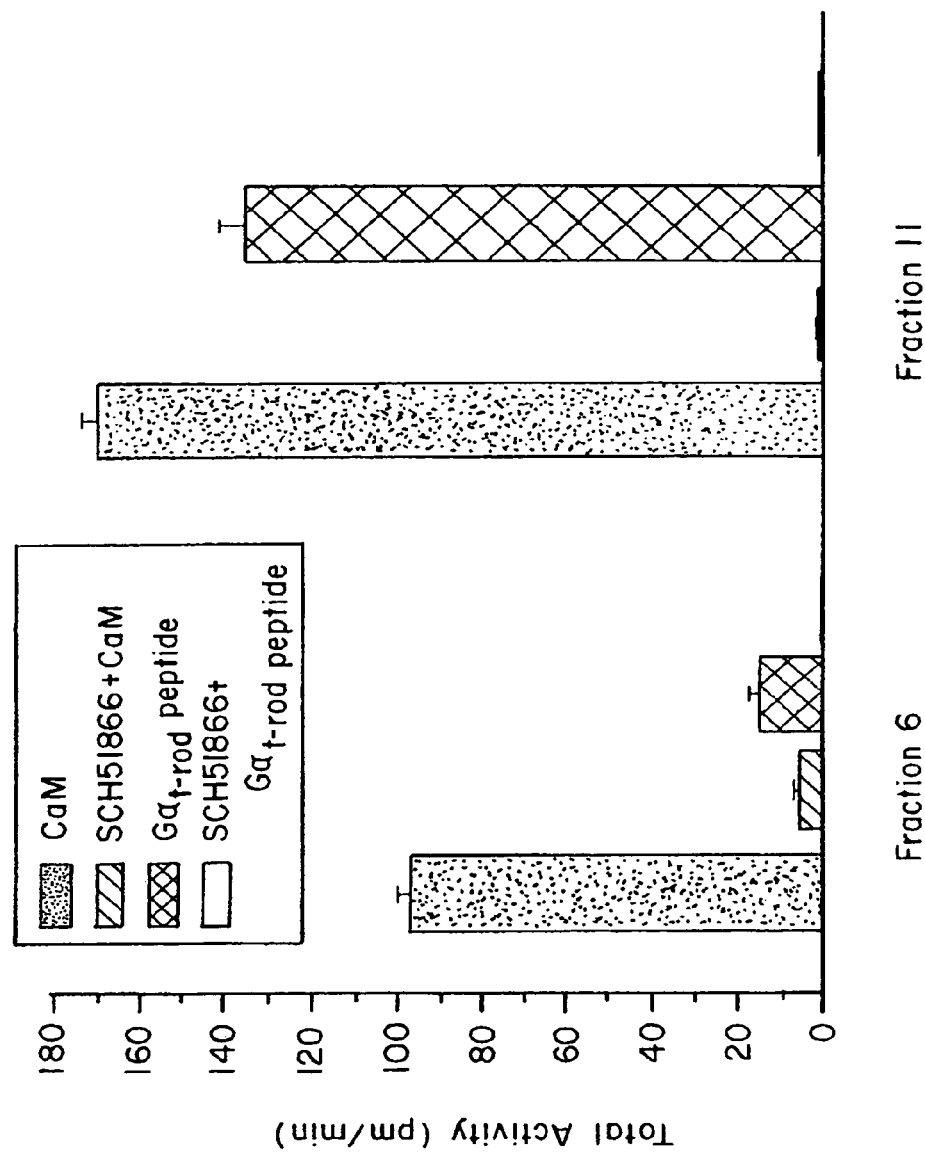

FIG. 4. The PDE 1A activity of fractions 6 and 11 (from the anion exchange fractions shown in FIGS. 1A and 1B was inhibited using SCH 51866 and the calmodulin and peptide activity remaining was assayed using 1 µM cGMP in the presence of 1 mM EGTA (open bars) or 1 mM $CaCl_2$ and 4 µg/ml CaM (filled bars) or 100 µM $G\alpha_{t\text{-}rod}$ peptide I (gray bars). SCH 51866 inhibited CaM (hayched bars) and $G\alpha_{t\text{-}rod}$ peptide (vertical bars) stimulated activity indicating that, both are contributed by PDE1A present in these fractions. All values represent mean plus or minus standard error of mean of three independent experiments performed in triplicate.

Figure 5:
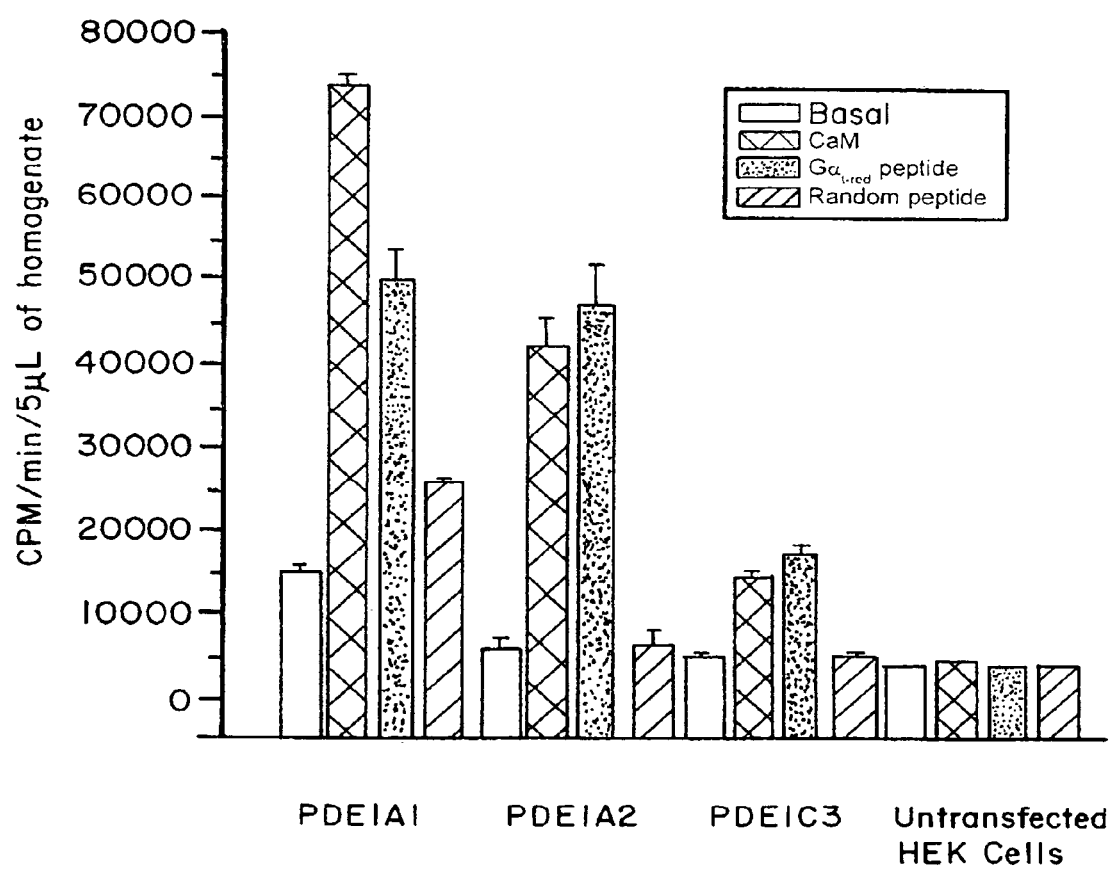

FIG. 5. PDE1A!, PDE1A2 and PDE1C3 were overexpressed in HEK-293 cells and PDE assays were performed using cGMP as a substrate in the presence of 1 mM EGTA (open bars), 1 mM $CaCl_2$ and 4 µg/ml CaM (hatched bars), 100 µM $G\alpha_{t\text{-}rod}$ polypeptide (black bars) or scrambled peptide (gray bars). Basal activity of untransfected HEK-293 cells was also determined in the presence of each of the above-listed compounds. All values depicted represent mean plus or minus standard error of mean from three independent experiments performed in duplicates.

FIG. 6 shows the amino acid sequence for one, exemplary transducin Gα protein (SEQ ID NO:1). See, also, FIGS. 1A–1B of U.S. Pat. No. 6,008,000 issued Dec. 28, 1999 as well as SEQ ID NO:23 of that patent.

5. DETAILED DESCRIPTION OF THE INVENTION

5.1. Definitions

The terms used in this specification generally have their ordinary meanings in the art, within the context of this invention and in the specific context where each term is used. Certain terms are discussed below, or elsewhere in the specification, to provide additional guidance to the practitioner in describing the devices and methods of the invention and how to make and use them.

General Definitions. As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting [FACS]). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

A "sample" as used herein refers to a biological material which can be tested for the presence of OSCAR polypeptides or OSCAR nucleic acids, e.g., to evaluate a gene therapy or expression in a transgenic animal or to identify cells, such as osteoclasts, that specifically express the OSCAR gene and its gene product. Such samples can be obtained from any source, including tissue, blood and blood cells, including circulating hematopoietic stem cells (for possible detection of protein or nucleic acids), plural effusions, cerebrospinal fluid (CSF), ascites fluid, and cell culture. In preferred embodiments samples are obtained from bone marrow.

Non-human animals include, without limitation, laboratory animals such as mice, rats, rabbits, hamsters, guinea pigs monkeys, etc.; domestic animals such as dogs and cats; and, farm animals such as sheep, goats, pigs, horses, and cows.

In preferred embodiments, the terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value.

Numerical quantities given herein are approximate unless stated otherwise, meaning that the term "about" or "approximately" can be inferred when not expressly stated.

The term "molecule" means any distinct or distinguishable structural unit of matter comprising one or more atoms, and includes, for example, polypeptides and polynucleotides.

Molecular Biology Definitions. In accordance with the present invention, there may be employed conventional molecular biology, microbiology and recombinant DNA techniques within the skill of the art. Such techniques are explained fully in the literature. See, for example, Sambrook, Fitsch & Maniatis, *Molecular Cloning: A Laboratory Manual,* Second Edition (1989) Cold Spring Harbor Laboratory Press, Cold Spring Harbor, N.Y. (referred to herein as "Sambrook et al., 1989"); *DNA Cloning: A Practical Approach,* Volumes I and II (D. N. Glover ed. 1985); *Oligonucleotide Synthesis* (M. J. Gaited. 1984); *Nucleic Acid Hybridization* (B. D. Hames & S. J. Higgins, eds. 1984); *Animal Cell Culture* (R. I. Freshney, ed. 1986); *Immobilized Cells and Enzymes* (IRL Press, 1986); B. E. Perbal, *A Practical Guide to Molecular Cloning* (1984); F. M. Ausubel et al. (eds.), *Current Protocols in Molecular Biology,* John Wiley & Sons, Inc. (1994).

The term "polymer" means any substance or compound that is composed of two or more building blocks ('mers') that are repetitively linked together. For example, a "dimer" is a compound in which two building blocks have been joined together; a "trimer" is a compound in which three building blocks have been joined together; etc.

The term "polynucleotide" or "nucleic acid molecule" as used herein refers to a polymeric molecule having a backbone that supports bases capable of hydrogen bonding to typical polynucleotides, wherein the polymer backbone presents the bases in a manner to permit such hydrogen bonding in a specific fashion between the polymeric molecule and a typical polynucleotide (e.g., single-stranded DNA). Such bases are typically inosine, adenosine, guanosine, cytosine, uracil and thymidine. Polymeric molecules include "double stranded" and "single stranded" DNA and RNA, as well as backbone modifications thereof (for example, methylphosphonate linkages).

Thus, a "polynucleotide" or "nucleic acid" sequence is a series of nucleotide bases (also called "nucleotides"), generally in DNA and RNA, and means any chain of two or more nucleotides. A nucleotide sequence frequently carries genetic information, including the information used by cellular machinery to make proteins and enzymes. The terms include genomic DNA, cDNA, RNA, any synthetic and genetically manipulated polynucleotide, and both sense and antisense polynucleotides. This includes single- and double-stranded molecules; i.e., DNA-DNA, DNA-RNA, and RNA-RNA hybrids as well as "protein nucleic acids" (PNA) formed by conjugating bases to an amino acid backbone. This also includes nucleic acids containing modified bases, for example, thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.) and alkylators to name a few. The polynucleotides may be derivatized by formation of a methyl or ethyl phosphotriester or an alkyl phosphoramidite linkage. Furthermore, the polynucleotides herein may also be modified with a label capable of providing a detectable signal, either directly or indirectly. Exemplary labels include radioisotopes, fluorescent molecules, biotin and the like. Other non-limiting examples of modification which may be made are provided, below, in the description of the present invention.

A "polypeptide" is a chain of chemical building blocks called amino acids that are linked together by chemical bonds called "peptide bonds". The term "protein" refers to polypeptides that contain the amino acid residues encoded by a gene or by a nucleic acid molecule (e.g., an mRNA or a cDNA) transcribed from that gene either directly or indirectly. Optionally, a protein may lack certain amino acid residues that are encoded by a gene or by an mRNA. For example, a gene or mRNA molecule may encode a sequence of amino acid residues on the N-terminus of a protein (i.e., a signal sequence) that is cleaved from, and therefore may not be part of, the final protein. A protein or polypeptide, including an enzyme, may be a "native" or "wild-type", meaning that it occurs in nature; or it may be a "mutant", "variant" or "modified", meaning that it has been made, altered, derived, or is in some way different or changed from a native protein or from another mutant.

"Amplification" of a polynucleotide, as used herein, denotes the use of polymerase chain reaction (PCR) to increase the concentration of a particular DNA sequence within a mixture of DNA sequences. For a description of PCR see Saiki et al., *Science* 1988, 239:487.

"Chemical sequencing" of DNA denotes methods such as that of Maxam and Gilbert (Maxam-Gilbert sequencing; see Maxam & Gilbert, *Proc. Natl. Acad. Sci. U.S.A.* 1977, 74:560), in which DNA is cleaved using individual base-specific reactions.

"Enzymatic sequencing" of DNA denotes methods such as that of Sanger (Sanger et al., *Proc. Natl. Acad. Sci. U.S.A.* 1977, 74:5463) and variations thereof well known in the art, in a single-stranded DNA is copied and randomly terminated using DNA polymerase.

A "gene" is a sequence of nucleotides which code for a functional "gene product". Generally, a gene product is a functional protein. However, a gene product can also be another type of molecule in a cell, such as an RNA (e.g., a tRNA or a rRNA). For the purposes of the present invention, a gene product also refers to an mRNA sequence which may be found in a cell. For example, measuring gene expression levels according to the invention may correspond to measuring mRNA levels. A gene may also comprise regulatory (i.e., non-coding) sequences as well as coding sequences. Exemplary regulatory sequences include promoter sequences, which determine, for example, the conditions under which the gene is expressed. The transcribed region of the gene may also include untranslated regions including introns, a 5'-untranslated region (5'-UTR) and a 3'-untranslated region (3'-UTR).

A "coding sequence" or a sequence "encoding" an expression product, such as a RNA, polypeptide, protein or enzyme, is a nucleotide sequence that, when expressed, results in the production of that RNA, polypeptide, protein or enzyme; i.e., the nucleotide sequence "encodes" that RNA or it encodes the amino acid sequence for that polypeptide, protein or enzyme.

A "promoter sequence" is a DNA regulatory region capable of binding RNA polymerase in a cell and initiation transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently found, for example, by mapping with nuclease S1), as well as protein binding domains (consensus sequences) responsible for the binding of RNA polymerase.

A coding sequence is "under the control of" or is "operatively associated with" transcriptional and translational control sequences in a cell when RNA polymerase transcribes the coding sequence into RNA, which is then trans-RNA spliced (if it contains introns) and, if the sequence encodes a protein, is translated into that protein.

The term "express" and "expression" means allowing or causing the information in a gene or DNA sequence to become manifest, for example producing RNA (such as rRNA or mRNA) or a protein by activating the cellular functions involved in transcription and translation of a corresponding gene or DNA sequence. A DNA sequence is expressed by a cell to form an "expression product" such as an RNA (e.g., a mRNA or a rRNA) or a protein. The expression product itself, e.g., the resulting RNA or protein, may also said to be "expressed" by the cell.

The term "transfection" means the introduction of a foreign nucleic acid into a cell. The term "transformation" means the introduction of a "foreign" (i.e., extrinsic or extracellular) gene, DNA or RNA sequence into a host cell so that the host cell will express the introduced gene or sequence to produce a desired substance, in this invention typically an RNA coded by the introduced gene or sequence, but also a protein or an enzyme coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell or cells of a different genus or species.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence. Vectors may include plasmids, phages, viruses, etc. and are discussed in greater detail below.

A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A large number of vectors, including plasmid and fungal vectors, have been described for replication and/or expression in a variety of eukaryotic and prokaryotic hosts. The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal).

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells such as Sf9, Hi5 or S2 cells and *Baculovirus* vectors, Drosophila cells (Schneider cells) and expression systems, and mammalian host cells and vectors.

The term "heterologous" refers to a combination of elements not naturally occurring. For example, the present invention includes chimeric RNA molecules that comprise an rRNA sequence and a heterologous RNA sequence which is not part of the rRNA sequence. In this context, the heterologous RNA sequence refers to an RNA sequence that is not naturally located within the ribosomal RNA sequence. Alternatively, the heterologous RNA sequence may be naturally located within the ribosomal RNA sequence, but is found at a location in the rRNA sequence where it does not naturally occur. As another example, heterologous DNA refers to DNA that is not naturally located in the cell, or in a chromosomal site of the cell. Preferably, heterologous DNA includes a gene foreign to the cell. A heterologous expression regulatory element is a regulatory element operatively associated with a different gene that the one it is operatively associated with in nature.

The terms "mutant" and "mutation" mean any detectable change in genetic material, e.g., DNA, or any process, mechanism or result of such a change. This includes gene mutations, in which the structure (e.g., DNA sequence) of a gene is altered, any gene or DNA arising from any mutation process, and any expression product (e.g., RNA, protein or enzyme) expressed by a modified gene or DNA sequence. The term "variant" may also be used to indicate a modified or altered gene, DNA sequence, RNA, enzyme, cell, etc.; i.e., any kind of mutant.

"Sequence-conservative variants" of a polynucleotide sequence are those in which a change of one or more nucleotides in a given codon position results in no alteration in the amino acid encoded at that position.

"Function-conservative variants" of a polypeptide or polynucleotide are those in which a given amino acid residue in the polypeptide, or the amino acid residue encoded by a codon of the polynucleotide, has been changed or altered without altering the overall conformation and function of the polypeptide. For example, function-conservative variants may include, but are not limited to, replacement of an amino acid with one having similar properties (for example, polarity, hydrogen bonding potential, acidic, basic, hydrophobic, aromatic and the like). Amino acid residues with similar properties are well known in the art. For example, the amino acid residues arginine, histidine and lysine are hydrophilic, basic amino acid residues and may therefore be interchangeable. Similar, the amino acid residue isoleucine, which is a hydrophobic amino acid residue, may be replaced with leucine, methionine or valine. Such changes are expected to have little or no effect on the apparent molecular weight or isoelectric point of the polypeptide. Amino acid residues other than those indicated as conserved may also differ in a protein or enzyme so that the percent protein or amino acid sequence similarity between any two proteins of similar function may vary and may be, for example, from 70% to 99% as determined according to an alignment schem such as the Cluster Method, wherein similarity is based on the MEGALIGN algorithm. "Function-conservative variants" of a given polypeptide also include polypeptides that have at least 60% amino acid sequence identity to the given polypeptide as determined, e.g., by the BLAST or FASTA algorithms. Preferably, function-conservative variants of a given polypeptide have at least 75%, more preferably at least 85% and still more preferably at least 90% amino acid sequence identity to the given polypeptide and, preferably, also have the same or substantially similar properties (e.g., of molecular weight and/or isoelectric point) or functions (e.g., biological functions or activities) as the native or parent polypeptide to which it is compared. As a specific example, TABLE 2 in the Examples, infra, lists several genes which are differentially expressed in either scotoma or peri-scotoma regions of the cerebral cortex and which may be used in the microarrays of the present invention. Many of these genes encode gene products (specifically, polypeptides) which have high levels of amino acid sequence identity to one or more polypeptides already known in the art, as indicated in column 3 of TABLE 2. These scotoma and peri-scotoma genes are therefore considered to be functional conservative variants of the genes that encode these known polypeptides.

The term "homologous", in all its grammatical forms and spelling variations, refers to the relationship between two proteins that possess a "common evolutionary origin", including proteins from superfamilies (e.g., the immunoglobulin superfamily) in the same species of organism, as well as homologous proteins from different species of organism (for example, myosin light chain polypeptide, etc.; see, Reeck et al., Cell 1987, 50:667). Such proteins (and their encoding nucleic acids) have sequence homology, as reflected by their sequence similarity, whether in terms of percent identity or by the presence of specific residues or motifs and conserved positions. For instance, column 3 in Table 2 presented in the Examples, infra, sets forth homologs of genes which are differentially expressed in either scotoma or peri-scotoma areas of the cerebral cortex, or in both scotoma and peri-scotoma areas of the cerebral cortex. Such homologs therefore may also be used in the methods and compositions of the present invention.

The term "sequence similarity", in all its grammatical forms, refers to the degree of identity or correspondence between nucleic acid or amino acid sequences that may or may not share a common evolutionary origina (see, Reeck et al., supra). However, in common usage and in the instant application, the term "homologous", when modified with an adverb such as "highly", may refer to sequence similarity and may or may not relate to a common evolutionary origin.

In specific embodiments, two nucleic acid sequences are "substantially homologous" or "substantially similar" when at least about 80%, and more preferably at least about 90% or at least about 95% of the nucleotides match over a defined length of the nucleic acid sequences, as determined by a sequence comparison algorithm known such as BLAST, FASTA, DNA Strider, etc. An example of such a sequence is an allelic or species variant of the specific genes of the present invention (e.g., the genes comprising the nucleotide sequences recited in Table 1 of the Examples, infra). Sequences that are substantially homologous may also be identified by hybridization, e.g., in a Southern hybridization experiment under, e.g., stringent conditions as defined for that particular system.

Similarly, in particular embodiments of the invention, two amino acid sequences are "substantially homologous" or "substantially similar" when greater than 80% of the amino acid residues are identical, or when greater than about 90% of the amino acid residues are similar (i.e., are functionally identical). Preferably the similar or homologous polypeptide sequences are identified by alignment using, for example, the GCG (Genetics Computer Group, Program Manual for the GCG Package, *Version* 7, Madison Wis.) pileup program, or using any of the programs and algorithms described above (e.g., BLAST, FASTA, etc.).

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin or a fluorescent dye (for example, Cy3 or Cy5) has been covalently conjugated.

In one embodiment, a labeled oligonucleotide can be used as a probe to detect the presence of a nucleic acid. For example, in preferred embodiments the nucleic acids of this invention are used as probes, e.g., on microarrays of the invention, to detect expression of certain genes in cells (e.g., in cells of a cerebral cortex or other brain tissue). In another embodiment, oligonucleotides (one or both of which may be labeled) can be used as PCR primers, either for cloning full length or a fragment of a nucleic acid, or to detect the presence of nucleic acids in cells. For instant, the Examples, infra, describe the design and use of PCR primers to amplify cDNA sequences in a cDNA library, for use on a microarray of the present invention.

In a further embodiment, an oligonucleotide of the invention can form a triple helix with an OSCAR DNA molecule. The present invention also provides antisense nucleic acids (including ribozymes), which may be used to inhibit expression of a gene or its gene product. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, triple helix interactions, ribozymes and RNase-H mediated arrest. Antisense nucleic acid molecules can be encoded by a recombinant gene for expression in a cell (e.g., U.S. Pat. Nos. 5,814,500; 5,811,234), or alternatively they can be prepared synthetically (e.g., U.S. Pat. No. 5,780,607). Other specific examples of antisense nucleic acid molecules of the invention are provided infra.

Generally, oligonucleotides are prepared synthetically, preferably on a nucleic acid synthesizer. Accordingly, oligonucleotides can be prepared with non-naturally occurring phosphoester analog bonds, such as thioester bonds, etc. Specific non-limiting examples of synthetic oligonucleotides envisioned for this invention include, in addition to the nucleic acid moieties described above, oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substitued silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15 M NaCl, 0.015 M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligoncucleotide molecules used. Exemplary temperatures may be 37° C. (for 14-base oligonucleotides), 48° C. (for 17-base oligoncucleotides), 55° C. (for 20-base oligonucleotides) and 60° C. (for 23-base oligonucleotides). Exemplary suitable hybridization conditions for oligonucleotides include washing in 6×SSC/ 0.05% sodium pyrophosphate, or other conditions that afford equivalent levels of hybridization.

5.2. Recombinant Expression Systems

A wide variety of host/expression vector combinations (i.e., expression systems) may be employed in expressing the DNA sequences of this invention, particularly in cells from tissue of the central nervous system such as the cerebral cortex. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., Gene 67:31–40, 1988), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2 m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. In addition, various tumor cells lines can be used in expression systems of the invention.

Yeast expression systems can also be used according to the invention to express any protein of interest. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with Pro-Bond resin and cleaved with enterokinase; Invitrogen), to mention just two, can be employed according to the invention.

Expression of the protein or polypeptide may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. Nos. 5,385,839 and 5,168,062), the SV40 early promoter region (Benoist and Chambon, 1981, Nature 290:304–310), the promoter contained in the 3' long terminal repeat of Rous sarcoma virus (Yamamoto, et al., Cell 22:787–797, 1980), the herpes thymidine kinase promoter (Wagner et al., Proc. Natl. Acad. Sci. U.S.A. 78:1441–1445, 1981), the regulatory sequences of the metallothionein gene (Brinster et al., Nature 296: 39–42, 1982); prokaryotic expression vectors such as the β-lactamase promoter (Villa-Komaroff, et al., Proc. Natl. Acad. Sci. U.S.A. 75:3727–3731, 1978), or the tac promoter (DeBoer, et al., Proc. Natl. Acad. Sci. U.S.A. 80:21–25, 1983); see also "Useful proteins from recombinant bacteria" in Scientific American, 242:74–94, 1980; and promoter elements from yeast or other fungi such as the Gal 4 promoter, the ADC (alcohol dehydrogenase) promoter, PGK (phosphoglycerol kinase) promoter, alkaline phosphatase promoter.

Preferred vectors, particularly for cellular assays in vitro and in vivo, are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 7:980–990, 1992). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 2:320–330, 1991), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest. 90:626–630, 1992; see also La Salle et al., Science 259:988–990, 1993); and a defective adeno-associated virus vector (Samulski et al., J. Virol. 61:3096–3101, 1987; Samulski et al., J. Virol. 63:3822–3828, 1989; Lebkowski et al., Mol. Cell. Biol. 8:3988–3996, 1988).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

5.3. Screening Assays

Using screening assays such as those described hereinbelow, it is possible for one skilled in the art to identify compounds that modulate (e.g., inhibit or enhance) activity of a phosphodiesterase. In particular, the Example infra demonstrates that a G-protein may interact with, and thereby activate, a phosphodiesterase polypeptide (PDE), such as a CaM-stimulated PDE.

PDEs are well known in the art, and a wide number of PDE polypeptides have been sequence and are publicly available. For reviews, see Beavo, *Adv. in Second Mess. and Prot. Phosph. Res.* 1988, 22:1–38; see also, Beavo, "Multiple Phosphodiesterase Isozymes: Background, Nomenclature and Implications", pp. 3–15 in *Cyclic Nucleotide Phosphodiesterases: Structure, Regulation and Drug Action* 1990, Beavo & Houslay, Eds., John Wiley & Sons, New York; Wang et al., "Calmodulin-Stimulated Cyclic Nucleotide Phosphodiesterases", pp. 19–59 in *Cyclic Nucleotide Phosphodiesterases: Structure, Regulation and Drug Action,* supra; and Manganiello et al., "Cyclic GMP-Stimulated Cyclic Nucleotide Phosphodiesterases", pp. 62–85 in *Cyclic Nucleotide Phosphodiesterases: Structure, Regulation and Drug Action,* supra. See, also, U.S. Pat. Nos. 6,037,119 and 6,015,677, issued Mar. 14, 2000 and Jan. 18, 2000, respectively, to Beavo et al. At least five distinct types or families of PDEs are known in the art, including: Type I or calmodulin (CaM)-stimulated PDEs; Type II or cGMP-stimulated PDEs; Type III or cGMP-inhibited PDEs; Type Iv or cAMP specific PDEs; and Type V or cGMP-specific PDEs. The PDEs from each of these five families are referred to herein as PDE1, PDE2, PDE3, PDE4 and PDE5, respectively.

Although the methods and compositions of the present invention may be practiced using any PDE polypeptide from any of the above classes of PDEs and from any species of organism, in preferred embodiments the invention is practiced using a CaM-stimulated PDE (i.e., a PDE1 polypeptide). Exemplary CaM-stimulated PDEs which may be used, and are preferred, include PDE1A (including isoforms thereof, such as PDE1A1 and PDE1A7) and PDE1C (as well as isoforms thereof). See, for example, the polypeptide sequences deposited in GenBank Accession Nos. NP_005010.1 (GI number 4826892), P54750 (GI number 1705942), AAC50436 (GI number 1151109), P14100 (GI number 544050), NP_005011 (GI number 4826894), Q14123 (GI number 2499445), AAC50437 (GI number 1151111) and AAA96961.1 (GI number 1151113), each of which was accessed on Sep. 13, 2000. PDE polypeptides from other families may also be used, however, including PDE2, PDE3, PDE4 (e.g., PDE4A) and PDE5 (e.g., PDE5A) polypeptides.

G-proteins are also well known in the art (for reviews, see Birnbaumer, *Ann. Rev. Pharmacol. Toxicol.* 1990, 30:675–705; and Simon et al., *Science* 1991, 252:802–808). Any subunit (e.g., an α-, β- or γ-subunit) of any G-protein from any species of organism may be used to practice the methods of the present invention, as well as any heterodimer of any subunit or subunits of G-proteins. The invention further contemplates the use of fragments of subunits (i.e., an α-, β-, or γ-subunit) of G-protein, particularly "effector fragments" which are described hereinbelow. However, because the α-subunit generally confers the most specificity of interaction between a G-protein and its effector, in preferred embodiments the methods and compositions of the present inventions are practiced using the α-subunit of a G-protein (i.e., a Gα polypeptide) or a fragment thereof. Exemplary G-proteins which may be used in the methods and compositions of the present invention include, but are not limited to, G-proteins that are expressed in taste cells, and in other signal transducing cells (for example rod and/or cone photoreceptor cells). As an example, and not by way of limitation, in one preferred embodiment the α-subunit of the G-protein gustducin is used in the methods and compositions of the present invention. In another exemplary embodiment the α-subunit of the G-protein transducin (e.g., from cone or rod photoreceptor cells) is used in the methods and compositions of the invention (see, for example U.S. Pat. No. 6,008,000 issued Dec. 28, 1999 to Margolskee and, in particular SEQ ID NOS:21–24 shown in FIGS. 1A–1B of that patent).

Without being limited to any particular mechanism, G-proteins are believed to interact with PDE polypeptides through the interaction of an "effector activation region" of the G-protein with the PDE. An "effector activation region" or "effector region", as the term is used herein, refers to a region or domain of a protein (e.g., of a G-protein or of a subunit thereof) that specifically binds to and thereby activates a PDE polypeptide. Thus, in particularly preferred embodiments of the invention, a polypeptide having an amino acid sequence of an effector activation region of a G-protein or of a G-protein subunit (e.g., an α-, β- or γ-subunit) is used. For example, the Example infra describes the use of a polypeptide having the amino acid sequence of residues 293–314 of a transducin Gα polypeptide (e.g., SEQ ID NO:23 in FIGS. 1A–1B of U.S. Pat. No. 6,008,000 issued Dec. 28, 1999 to Margolskee). Preferably, the polypeptide having an amino acid sequence of an effector activation region for a G-protein or a G-protein subunit comprises a sequence of between about 10 and about 50 amino acids from the polypeptide sequence of the G-protein or G-protein subunit. In particularly preferred embodiments, the polypeptide comprises a sequence of about 20 amino acid residues from the sequence of the G-protein or G-protein subunit.

Classes of compounds that may be identified by such screening assays include, but are not limited to, macromolecules as well as small molecules (e.g., organic or inorganic molecules which are less than about 2 kd in molecular weight, are more preferably less than about 1 kd in molecular weight, and/or are able to cross the blood-brain barrier or gain entry into an appropriate cell and affect an interaction between a G-protein and a PDE polypeptide). Compounds identified by these screening assays may also include peptides and polypeptides. For example, the screening assays may identify soluble peptides, fusion peptides, members of combinatorial libraries (such as ones described by Lam et al., *Nature* 1991, 354:82–84; and by Houghten et al., *Nature* 1991, 354:84–86), members of libraries derived by combinatorial chemistry (for example, molecular libraries of D- and/or L-configuration amino acids), and phosphopeptides (for example, members of random or partially degenerate, directed phosphopeptide libraries such as those described in Songyang et al., *Cell* 1993, 72:767–778). The screening methods of the invention may also identify antibodies that affect an interaction between a G-protein and a PDE polypeptide, including but not limited to polyclonal, monoclonal, humanized, anti-idiotypic, chimeric or single chain antibodies, as well as antibody fragments such as FAb, F(Ab')$_2$, FAb expression library fragments and epitope binding fragments thereof.

In general, assays for identifying compounds that interfere with the interaction between a PDE polypeptide (particularly a CaM-stimulated PDE) and an effector activation polypeptide involve preparing a test reaction mixture that contains the PDE polypeptide and the effector activation polypeptide under conditions and for a time-sufficient for the PDE polypeptide and the effector activation polypeptide to bind and form a complex. In order to test a compound for inhibitory activity (i.e., for the ability to inhibit formation of the complex, or to disrupt the binding complexes once formed), the test compound preferably is also present in the reaction mixture. In one exemplary embodiment, the test compound may be initially included in the test reaction mixture with the PDE and effector activation polypeptides. Alternatively, however, the test compound may be added to the test reaction mixture at a later time, subsequent to the addition of the PDE and effector polypeptides. In preferred embodiments, one or more control reaction mixtures, which do not contain the test compound, may also be prepared. Typically, a control reaction mixture will contain the same PDE and effector activation polypeptides that are in the test reaction mixture, but will not contain a test compound. A control reaction mixture may also contain a placebo, not present in the test reaction mixture, in place of the test compound.

The formation of a complex between the PDE and effector polypeptides may then be detected in the reaction mixture. The formation of such a complex in the absence of the test compound (e.g., in a control reaction mixture) but not in the presence of the test compound, indicates that the test compound is one which interferes with or modulates the interaction of a PDE polypeptide and an effector polypeptide.

Assays for compounds that modulate the interaction of a PDE polypeptide and an effector polypeptide may be conducted in a heterogenous format or, alternatively, in a homogeneous format. Heterogeneous assays typically involve anchoring either a PDE polypeptide or an effector polypeptide onto a solid phase and detecting compounds anchored to the solid phase at the end of the reaction and after removing (e.g., by washing) unbound compounds.

For example, in one preferred embodiment of such a method, a PDE polypeptide may be anchored onto a solid surface and a labeled effector polypeptide is contacted to the surface. In order to test a compound for inhibitory activity, the test compound preferably is also contacted to the surface. For example, the test compound may be contacted to the surface with the labeled effector polypeptide. Alternatively, the test compound may be contacted to the surface at a later time, subsequent to introduction of the effector polypeptide.

After contacting the effector polypeptide to the surface, the PDE and effector polypeptides are incubated for sufficient time and under sufficient conditions that a complex may form between the PDE and effector polypeptides. In embodiments where a test compound is contacted to the surface with the effector polypeptide, the PDE and effector polypeptides are incubated with the test compound. Alternatively, in embodiments where a test compound is contacted to the surface at a time subsequence to the introduction of the effector polypeptide, the PDE and effector polypeptides may be incubated before addition of the test compound, for a sufficient time and under sufficient conditions that a complex may form between the PDE and effector polypeptides. In such an alternatively embodiment, the PDE and effector compounds are preferably incubated again with the test compound (preferably under the same conditions), e.g., so that the test compound may disrupt complexes between the PDE and effector polypeptides that have formed, e.g., during the first incubation. After incubating the polypeptides and test compound, unbound molecules of the effector polypeptides and test compound are removed from the surface (e.g., by washing) and labeled molecules which remain are detected.

As noted supra, in preferred embodiments one or more control reactions which do not contain a test compound may also be prepared. For example, the PDE polypeptide may be attached to a solid support or surface and a labeled effector polypeptide contacted thereto, without also contacting the test compound to the surface. Alternatively, a placebo may be contacted to the surface instead of the test compound. The above-described heterogenous assay may also be performed by attaching an effector polypeptide to a solid support or surface, and contacting a labeled PDE polypeptide thereto.

The polypeptides may be labeled according to any means known in the art including, but not limited to, radiolabeling with iodine or phosphorous (see, for example, European Patent No. EP 372707 B), fluroescent dyes (e.g., Cy3 or Cy5), a chelating group complexed with a metal ion, a chromophore, a fluorophore, biotin, a gold colloid, etc.

Alternatively, because interaction between PDE polypeptides of the invention and an effector polypeptide (e.g., a G-protein) activate PDE, the screening assays of the present invention may also identify compounds which modulate an interaction between a PDE polypeptide and an effector polypeptide by detecting changes in PDE activity. In a preferred embodiment, changes in PDE activity are detected by detecting hydrolysis of a cyclic nucleotide monophosphate (cNMP) such as cAMP or cGMP. Routine assays for detecting PDE activity (e.g., by detecting cNMP hydrolysis) are well known in the art and have been described, e.g., by Sonnenburg et al. (*Methods* 1998, 14:3–19). The exemplary use of such assays is also described in the Example, infra. Such assays are preferably used to detect PDE activity in a homogenous assay system. However, those skilled in the art can readily appreciate that such assays may also be adapted for use in a heterogenous assay system, such as those described above, without undue experimentation.

The screening methods of the present invention also include methods for identifying PDEs that are activated by a G-protein. Such methods comprise detecting activation of a PDE polypeptide contacted with a polypeptide. The polypeptide comprises a G-protein activation peptide from an a-domain of a G-protein. In one embodiment, the polypeptide is a G-protein. The G-protein/PDE can be expressed in a heterologous cell, where PDE activity can be detected by any of the standard measures. Alternatively, purified G-protein polypeptide or peptide and PDE can be combined in vitro, and PDE activity determined using routine methods. In yet another embodiment, the G-protein peptide can be added to a cell containing a PDE for testing to determine whether it activates the PDE. Such peptides can be at least about 20 amino acid residues, e.g., such as the peptide comprising amino acid residues 293–314 of the transducin-α subunit, more particularly a peptide having a sequence as set forth in FIG. 6 (SEQ ID NO:1).

This aspect of the invention permits evaluating the ability of any G-protein to interact and modulate the activity of any PDE, e.g., a Type I PDE, a Type II PDE, Type III PDE, a Type IV PDE, and a Type V PDE. In addition to each of these PDE types, each of the sub-types and isotype (e.g., splice variants) can be measured. Preferably the PDE is a calmodulin-activated PDE. Specific examples describe such an interaction with a series of Type I and one Type V PDEs.

Although any G-protein can be used, in specific examples the G-protein is selected from the group consisting of transducin and gustucin.

Once such interactions have been identified, the present invention permits generation of assay systems and methods that harness the specific G-protein/PDE combination to discover compounds that inhibit G-protein-mediated PDE activity. As discussed above, such compounds clearly have potential for treatment of diseases or disorders associated with defect in PDE activity.

6. EXAMPLE

The invention is also described by means of the following particular example. In particular, the experiments described in this example identify and confirm the existence of a direct interaction between certain phosphodiesterases (PDAs) and G-proteins. In particular, these experiments demonstrate that an effector polypeptide comprising an amino acid sequence of a G-protein can interact with, and thereby modulates, activity of phosphodiesterases, particularly CaM-stimulated PDEs such as PDE1A (including isoforms thereof, such as PDE1A1 and PDE1A7) and PDE1C.

The use, however, of this or other examples anywhere in the specification is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

6.1. Materials and Methods

Reagents. Leupeptin and aprotinin were obtained from Boehringer-Mannheim Biochemicals (Indianapolis, Ind.). The DEAE anion exchange column was from Bio-Rad laboratories (Hercules, Calif.). Horseradish peroxidase (HRP)-conjugated goat anti-rabbit IgG was purchased from Amersham. [8,5$^3$H] cGMP and [$^3$H]cAMP were purchased from NEN-Research Products (Boston, Mass.). Taq DNA polymerase dye terminator cycle sequencing ready reaction DNA sequencing kits were from Perkin-Elmer Corp. (Foster City, Calif.). The 100 bp ladder and prestained protein markers were from GIBCO-BRL (Gaithersburg, Md.). Calmodulin affinity beads were purchased from Pharmacia Biotech (Piscataway, N.J.). Bovine brain calmodulin was purchased from Calbiochem Corp. (La Jolla, Calif.). All the peptides in the study were synthesized at the HHMI Protein Core facilities of Columbia University or the University of Washington. All other reagents were purchased from Sigma Chemical Co. (St. Louis, Mo.).

Preparation of taste extract. 1–2 gm circumvallate taste papillae or fungiform papillae from fresh bovine tongues were dissected and homogenized in a buffer containing 20 mMTris-Cl pH 7.5, 1 mM EDTA, 1 mM DTT, 10% glycerol, 10 µg/ml leupeptin, 10 µg/ml aprotinin, 100 µM AEBSF and 10 µg/ml pepstatin. Homogenization was carried out using a Polytron homogenizer. The homogenate was first spun at 2500×g for 10 minutes at 4° C. and the resulting supernatant was spun at 100,000×g for 30 minutes at 4° C. The supernatant of the second spin was checked for PDE activity and fractionated by anion exchange chromatography.

Anion Exchange Chromatography. Supernatant prepared from taste papillae was loaded at 1 ml/min on a DEAE-10 anion exchange column which had been equilibrated with buffer A (20 mM Tris-HCl pH 7.5, 2 mM EDTA, 20 mM β-mercapto ethanol). The column was washed in buffer A for 15 minutes or until protein was no longer detected in the buffer. Bound protein activity was eluted at a flow rate of 2 ml/min with a linear gradient (0–100%) of buffer B (buffer A+1 M NaCl) over 45 minutes Fractions were collected at 4° C. and assayed for PDE Activity. Aliquots of each fraction were boiled in sample buffer for Western blot analysis.

PDE Assays and CaM Affinity on Beads. PDE assays followed established procedures (Sonnenburg et al., *Methods* 1998, 14:3–19). All assays were performed at 30° C. using either 1 µM cAMP or between 0.2 and 1 µM cGMP as substrate in the presence of 1 mM EGTA (basal), 1 mM $CaCl_2$ plus 4 µg/ml CaM ($Ca^{2+}$/CaM) or 100 µM effector activation peptide ($G\alpha_{t-rod}$) peptide.

Fractions containing $Ca^{2+}$/CaM stimulable activity were further affinity purified using Calmodulin-sepharose 4B beads in a buffer containing 40 mM Tris-HCl pH 7.5, 0.1 mM $CaCl_2$, 3 mM Mg acetate, 100 mM NaCl and 10 mM β-mercaptoethanol in the presence of 10 µg/ml leupeptin and 10 µg/ml Soybean trypsin inhibitor (SBTI). Specificity of the calmodulin affinity beads was checked by doing an affinity chromatography purification in the presence of 2 mM EGTA instead of $CaCl_2$. The beads were incubated with the appropriate fractions at 4° C. for 1 hour, then spun for 2 minutes and the supernatant and pellet kept separately. The beads were then washed in the same buffer and resuspended in the presence of protease inhibitors. PDE activity was checked on the beads and in the supernatant. $CaCl_2$ was compensated in the PDE assays when the CaM affinity was done in presence of excess EGTA.

Over-expression and Assay of Recombinant PDEs. HEK 293 cells were cultured in Eagle's MEM with 2 mM glutamate, Earle's balanced salt solution, 1.5 g/L sodium bicarbonate, 0.1 mM non-essential amino acids, 1 mM sodium pyruvate, and 10% heat-inactivated fetal calf serum. HEK 293 cells were seeded at 0.5×10$^6$ per well in a 6 well dish. After 24 hours, cells were transfected with DNA constructs using Gene Porter (Gene Therapy Systems), a lipid-based transfection reagent. Cells were transfected with 6 µg DNA (PDE1A1, PDE1A2 or PDE1C3) and 30 µl transfection reagent in serum free media in a volume of 1 ml. After 5 hours, the cells were supplemented with 1 ml media containing twice serum. 24 hours later, the cells were harvested by rinsing twice with PBS, scraping the cells into 200 µl of buffer containing 20 mM Tris-Cl pH 7.5, protease inhibitors (Sigma P- 8340), 1 mM 4-(2-aminoethyl) benzenesulfonyl fluoride (AEBSF), 15 μM pepstatin A, 14 μM trans-epoxysuccinyl-L-leucylamido(4-guanidino) butane (E-64), 40 μM bestatin, 22 μM leupeptin, and 0.8 μM aprotinin. Cells were sonicated in 3 five second bursts at approximately 10 Watts, and the lysates were used as the source of enzyme in the PDE assay.

Western Blot Analysis. Samples were boiled in sample buffer for 5 minutes, loaded onto an SDS-polyacrylamide gel (10% acrylamide/0.2% bisacrylamide) and electrophoresed. The separated proteins were transferred to a nitrocellulose membrane and immunostained with isoenzyme-specific anti-PDE1 or PDE5 antibodies (Ausubel et al. (eds.), *Current Protocols in Molecular Biology*, John Wiley & Sons, Inc., 1994). The immuno-reactivity was detected by enhanced chemiluminescence using HRP-conjugated goat anti-rabbit IgGs and HRP-luminescent substrate mixture.

Polymerase Chain Reaction Amplification of PDEs. PCRs were set up using specific primers for the various PDE isoforms and a cDNA library from bovine circumvallate papillae as template. The reaction products were separated on a 1% low melting point agarose gel containing ethidium bromide. DNA bands of the predicted sizes, based on the published sequence and location of the amplification primers, were gel eluted and sequenced using dye terminator cycle sequencing.

Peptide Synthesis. The $G\alpha_{t\text{-}rod}$ peptide corresponding to the PDE effector-interaction-region of rod transducin, was synthesized by the solid phase Fmoc/t-Bu Chemistry method using 431A Applied Biosystems synthesizer. A scrambled peptide of the same amino acid composition, but of random sequence was also synthesized. Both peptides were synthesized with a free amino terminus and with an amide at the C-terminus. Crude peptides were purified by reversed phase HPLC on a 2.3×30 cm Bondapack C-18 column. The peptides were eluted at a flow rate of 8 ml/min. with a linear gradient (5–65% acetonitrile containing 0.1% trifluroacetic acid) over three hours, with detection at 215 nm. The purified peptides were dissolved in distilled water as 5 mM solutions and then stored at −20° C. prior to use.

Immunocytochemical Localization of PDEs. Frozen sections (8 μm) of murine lingual tissue previously fixed in 4% paraformaldehyde and cryoprotected in 20% sucrose were blocked in 3% BSA, 0.3% Triton X-100, 2% goat serum and 0.1% sodium azide in PBS for 1 h at room temperature. Double labeling of the sections was done using polyclonal antibodies against PDE1A (Sonnenburg et al., *Methods* 1998, 14:3–19) and $G\alpha_{gus}$ (Ruiz-Avila et al., *Nature* 1995, 14:3–19) according to a procedure supplied by Jackson Immunoresearch. The secondary antibodies were Cy3-conjugated goat-anti-rabbit (GAR) Fab for PDE1A and fluorescein-conjugated goat-anti-rabbit (GAR) Fab for $G\alpha_{gus}$. After blocking, the sections were incubated in succession with the following reagents: (1) PDE1A antisera (1:200); (2) GAR-Cy3 labeled Fab fragments; (3) unlabeled anti-rabbit antisera (to insure that all rabbit sites are occupied); (4) $G\alpha_{gus}$ antisera (1:1000); and (5) GAR-FITC labeled Fab fragments. The sections were washed three times with PBS containing 0.3% Triton-X 100 between each incubation. Since both primary antibodies were raised in rabbit, a control was performed in which the second primary antisera (i.e., anti-$G\alpha_{gus}$) was omitted to verify that the second labeled secondary antisera (GAR-FITC Fab) was not binding to the first primary antisera (i.e., anti-PDE1A). In additional controls, the immunoreactivity of PDE1A antibodies was blocked by preincubation with the antigen (GST-PDE1A C-terminal region fusion protein).

6.2. Results

Fractionation and Identification of Taste PDEs. To identify which, if any, PDEs in taste tissue are regulated by G-proteins such as transducin and gustducin (see U.S. Pat. No. 6,008,000 issued Dec. 28, 1999 to Margolskee), the PDE isoforms expressed in bovine taste tissue were resolved by anion-exchange chromatography. Each fraction was assayed for PDE activity in the presence of $Ca^{2+}$/CaM (calmodulin stimulable activity), EGTA (basal activity) or $G\alpha_{t\text{-}rod}$ peptide (transducin/gustducin stimulated activity) using either cGMP or cAMP as substrates. Western blot analysis of the fractions with PDE-specific antibodies was also performed.

A typical fractionation profile of cGMP hydrolysis activity, revealing multiple peaks, is shown in FIG. 1A. Although $Ca^{2+}$/CaM stimulated PDE activity predominates, there is significant basal PDE activity in the presence of EGTA, indicating the presence of PDEs which are not stimulated by $Ca^{2+}$/CaM. In general, the peaks of $Ca^{2+}$/CaM stimulated PDE activity overlap quite well with those of $G\alpha_{t\text{-}rod}$ peptide stimulated PDE activity. Four major peaks of cGMP PDE activity can be seen (FIG. 1A). The first small peak of cGMP hydrolytic activity (fractions 6–7) is likely to contain a $Ca^{2+}$/CaM stimulated PDE exclusively as is evident from the negligible phosphodiesterase activity in presence of EGTA. This peak was also activated by the $G\alpha_{t\text{-}rod}$ peptide. The second and the largest peak of cGMP hydrolytic activity (fractions 10–12) is also activated by both $Ca^{2+}$/CaM and $G\alpha_{t\text{-}rod}$ peptide, but also contains minimal basal cGMP hydrolytic activity in presence of EGTA. The third peak (fractions 13–15) shows greatest activity when stimulated by either $Ca^{2+}$/CaM or $G\alpha_{t\text{-}rod}$ peptide. However, this third peak also contains significant cGMP hydrolytic activity in presence of EGTA, indicating the presence of other PDEs that are not stimulated by $Ca^{2+}$/CaM. The fourth peak (fractions 21–23) was not stimulated above the basal level by either $Ca^{2+}$/CaM or $G\alpha_{t\text{-}rod}$ peptide.

A typical profile of cAMP hydrolysis by the same fractions is shown in FIG. 1B. Once again, four peaks of PDE activity can be seen. The first three peaks (fractions 6–7; fractions 10–12; fractions 13–15), which correspond well to those seen in FIG. 1A (i.e., with cGMP as substrate), show stimulation with either $Ca^{2+}$/CaM or $G\alpha_{t\text{-}rod}$ peptide, but display minimal basal activity in presence of EGTA. The fourth peak (fractions 19–23), however, exhibits substantial cAMP hydrolyzing activity (along with minimal cGMP hydrolyzing activity, see FIG. 1A) in presence of EGTA. The cAMP hydrolyzing activity of this forth peak is neither $Ca^{2+}$/CaM nor $G\alpha_{t\text{-}rod}$ peptide dependent. Based on its pharmacological properties with the PDE4 specific inhibitors rolipran and Ro-20-174, the PDE contained in these fractions (i.e., fractions 19–23) was identified as PDE4. This result is consistent with earlier cloning of two PDE4s from rat taste tissue (Spickofsky et al., *Nat. Struct. Biol.* 1994, 1:771–781).

To understand the specificity of the $G\alpha_{t\text{-}rod}$ peptide mediated stimulation of PDE activity, a scrambled peptide was synthesized which had the same amino acid composition as the $G\alpha_{t\text{-}rod}$ peptide. The ability of this scrambled peptide to activate PDEs in fractions 6 and 11 (which have the highest $G\alpha_{t\text{-}rod}$ peptide stimulated PDE activity) was then tested. The results of these tests are shown in FIG. 1C. The PDE activities of both fractions 6 and 11 are stimulated by the presence of the $G\alpha_{t\text{-}rod}$ peptide (hatched bars), but not by the scrambled peptide (gray bars). Thus, the interaction of the transducin peptide with these PDEs is not a non-specific phenomenon based on net charge. Rather, these data suggest that the $G\alpha_{t\text{-}rod}$ peptide binds specifically with the PDEs in a sequence dependent manner.

As is evident from FIGS. 1A and 1B, multiple PDEs are present in taste tissue, including $Ca^{2+}$/CaM-dependent and independent forms. To identify the $Ca^{2+}$/CaM dependent (i.e., CaM-stimulated) PDEs, Western blot analysis was performed using PDE 1 isoform specific antibodies (Rybalkin et al., *J. Clin. Invest.* 1997, 100:2611–2621). The first three peaks of $Ca^{2+}$/CaM stimulated cGMP hydrolytic activity (corresponding to fractions 6–7; 10–12 and 13–15 shown in FIG. 1A), immunoreact with PDE1A antibodies. Based on SDS PAGE mobility the first peak (fraction 6 and 7), with a band of ~50 kDa, contains a recently identified referred to as the PDE1A7 isoform (Accession number AF 59298). Fractions 11–14 contain an approximately 59 kDa molecular weight splice variant, corresponding in size to PDE1A1. An immunoblot of fractions 14–16 revealed detectable bands of PDE 1C splice variants in these fractions. In the absence of the stimulating peptide or $Ca^{2+}$/CaM, fractions 13–15 hydrolyze cGMP with a high degree of selectivity over cAMP, indicating the presence in these fractions of a cGMP specific PDE such as PDE5. Immunoblots of these fractions confirmed that the do, indeed, contain a cGMP specific PDE. Specifically, the fractions immunoreact with PDE5A specific antibodies (Bakre et al., *J. Cellular. Biochem.* 2000, 77:159–167).

These results therefore show that taste tissue contains multiple PDE activities, including CaM-stimulated PDE activity, e.g., from PDE1A1, PDE1A7 and PDE1C. In addition, anion exchange chromatography fractions which exhibit CaM-stimulated PDE activity also exhibit PDE activity stimulated by the $G\alpha_{t\text{-}rod}$ The taste tissue also contains PDE activity from other classes of PDEs, including PDE4 and PDE5. The presence of mRNA encoding each of these classes of PDEs was confirmed by RT-PCR using specific primers corresponding to unique regions of each isoform PDE1A, PDE1C, PDE4A and PDE5A followed by DNA sequencing. No product was observed for PDE1B.

A major part of the cGMP hydrolytic activity present in taste tissue extracts was not dependent on $Ca^{2+}$/CaM (FIG. 1A). Moreover, the Western blot analysis of fractions 13–16 showed immunostaining with a PDE5 antibody of a band of the appropriate molecular weight for PDE5. To confirm this result, a PDE5 specific antibody was used to immunoprecipitate the cGMP hydrolytic activity from fraction 14, the fraction with maximum cGMP hydrolytic activity in the presence of EGTA. Protein A beads were preincubated with (Ab beads) or without (control beads) primary anti-PDE5 antibody. PDE activity present on the beads was then determined using cGMP as the substrate in presence of EGTA (FIG. 2). The beads removed 60% of the activity when immunoprecipitation was performed in the presence of primary antibody (hatched bars) and the supernatant had little activity left (black bars). When the immunoprecipitation was performed in the absence of primary antibody (control beads), the bulk of the phosphodiesterase activity remained in the supernatant (gray bars) and the beads/pellet contained negligible activity. Thus, in addition to hydrolytic activity from PDE1, part of the cGMP hydrolytic activity measured in taste tissue is contributed by PDE5.

PDE1A isoforms are present in taste tissue. To confirm the presence of PDE1 A in the above described fractions from taste tissue, a CaM affinity "pulldown" assay was performed on those fractions in each peak, which showed the greatest $Ca^{2+}$/CaM stimulation over EGTA. Fraction 11 was incubated with CaM-sepharose 4B beads in presence of either $CaCl_2$ (CaM beads) or EGTA (EGTA beads) (FIG. 3). The supernatants and the PDE bound to the beads (pellets) were checked for cGMP PDE activity in presence of EGTA (open bars), $Ca^{2+}$/CaM (hatched bars) or $G\alpha_{t\text{-}rod}$ peptide (filled bars). With the CaM beads, 70–80% of the calmodulin or $G\alpha_{t\text{-}rod}$ peptide stimulable PDE activity originally observed in fraction 11 was present in the pellet, while the supernatant was nearly devoid of any PDE activity. The buffer in which the CaM beads were washed had negligible PDE activity. In the case of EGTA beads, less than 10% of the activity was present in the pellet and the bulk of the PDE activity was instead found in the supernatant, demonstrating the specificity and affinity for CaM of the interaction of the PDE in fraction 11. Similar results were obtained when the above experiment was done with fraction 6. The identification of fraction 11 as PDEIA was confirmed by Western blot of the CaM beads pellet.

SCH 51866 is, by far, one of the most specific inhibitors of PDE1 and inhibits PDE 1 and PDE5 with an $IC_{50}$ of 0.1 μM (Yan et al., *J. Biol. Chem.* 1996, 271:25699–2706). Inhibition of the $Ca^{2+}$/CaM-or $G\alpha_{t\text{-}rod}$ peptide stimulated PDE1A present in fractions 6 and 11 was therefore tested with SCH 51866. As shown in FIG. 4, fractions 6 and 11 showed low basal activity in presence of EGTA (open bars) when compared to calmodulin stimulated (filled bars) and peptide stimulated (gray bars). As expected, SCH 51866 inhibited calmodulin stimulated activity by 90% (hatched bars). Interestingly, SCH 51866 also inhibited peptide stimulated activity (vertical bars) present in the fraction. SCH 51866 also inhibited peptide stimulated activity of PDE1A bound to calmodulin beads; Thus, calmodulin and $G\alpha_{t\text{-}rod}$ peptide stimulated PDE activity is contributed by the same PDE, which is inhibited by SCH 51866. These results confirm that PDE1A, which is present in taste tissue, is indeed responsible for the $G\alpha_{t\text{-}rod}$ peptide stimulated activity.

Activation of PDE1 isoforms by the $G\alpha_{t\text{-}rod}$ peptide. The extensive overlap in $Ca^{2+}$/CaM stimulated and $G\alpha_{t\text{-}rod}$ peptide stimulated PDE activities in the chromatogram (FIG. 1) and in the CaM beads pellet (FIG. 3), discussed above, suggests that PDE1A expressed in taste tissue can be activated by either $Ca^{2+}$/CaM or the $G\alpha_{t\text{-}rod}$ peptide. To this hypothesis recombinant PDE1 isoforms were over expressed in HEK-293 cells and PDE activity of the cell homogenates was measured in the presence of either $G\alpha_{t\text{-}rod}$ peptide or $Ca^{2+}$/CaM (FIG. 5). All three recombinant PDEs, were stimulated by $Ca^{2+}$/CaM (hatched bars) and the $G\alpha_{t\text{-}rod}$ peptide (black bars), consistent with the hypothesis that Type I PDEs are indeed stimulated by the $G\alpha_{t\text{-}rod}$ peptide. The random (scrambled) peptide (gray bars) did not stimulate the recombinant PDEs except for PDE1A1, where only a modest activation, well below that achieved with either $Ca^{2+}$/CaM or the $G\alpha_{t\text{-}rod}$ peptide, was observed.

Expression of PDE1A in Taste Receptor Cells. So that the biological relevance of the above described findings could be better ascertained, immunocytochemistry was performed on taste bud sections from mouse circumvallate with antisera to $G\alpha_{gus}$ and PDE1A. In particular, these experiments determined whether PDE1A isoforms are expressed in taste receptor cells and, if so, whether those cells are also $G\alpha_{gus}$ positive.

As expected, $G\alpha_{gus}$ staining was observed in about one third of the cells in a taste bud. PDE1A staining was observed in the taste buds of about half the taste cells, confirming the presence of PDE1A in taste cells. When the two images are merged, three populations of cells can be identified: (1) $G\alpha_{gus}$/PDE1A doubly positive cells; (2) $G\alpha_{gus}$ singly positive cells; and (3) PDE1A singly positive cells. The majority of Gα$_{gus}$ cells were positive for PDE1A, consistent with the idea that Gα$_{gus}$ activated PDE1A during taste transduction. The PDE1A immunofluorescence was found in the perinuclear region as well as in the apical processes in the taste pore. The apical distribution is consistent with a role in taste transduction. The perinuclear pattern has been noted previously in cardiac cells expressing PDE1A (Rybalkin et al. *J. Clin. Invest.* 1997, 100:2611–2621).

---

What is claimed is:

1. A method for identifying a compound that modulates activity of a Type I phosphodiesterase (PDE), which method comprises:
   (a) contacting an effector activation polypeptide to a Type I PDE polypeptide under conditions that permit binding of the effector activation polypeptide to the PDE polypeptide, the effector activation polypeptide comprising an effector activation region of a G-protein; and
   (b) detecting binding of the effector activation polypeptide to the PDE polypeptide in the presence and in the absence of a test compound,
wherein the test compound is identified as a compound that modulates activity of a Type I PDE if binding of the effector activation polypeptide to the PDE polypeptide is modulated in the presence of the test compound.

2. The method of claim 1 wherein the test compound is identified as a compound that inhibits activity of a Type I PDE if binding of the effector activation polypeptide to the PDE polypeptide decreases in the presence of the test compound.

3. The method of claim 1 wherein the test compound is identified as a compound that enhances activity of a Type I PDE if binding of the effector activation polypeptide to the PDE polypeptide increases in the presence of the test compound.

4. A method for identifying a compound that modulates activity of a Type I phosphodiesterase (PDE), which method comprises:
   (a) contacting an effector activation polypeptide to a Type I PDE polypeptide, the effector activation polypeptide comprising an effector activation region of a G-protein; and
   (b) detecting PDE activity in the presence and in the absence of a test compound,
wherein the test compound is identified as a compound that modulates activity of a Type I PDE if PDE activity is modulated in the presence of the test compound.

5. The method of claim 4 wherein the test compound is identified as a compound that inhibits activity of a Type I PDE if PDE activity decreases in the presence of the test compound.

6. The method of claim 4 wherein the test compound is identified as a compound that enhances activity of a Type I PDE if PDE activity increases in the presence of the test compound.

7. The method of claim 4 wherein PDE activity is detected according to a method which comprises detecting hydrolysis of a cyclic nucleotide triphosphate (cNMP).

8. The method of claim 7 wherein the cNMP is selected from the group consisting of cAMP and cGMP.

9. The method of claim 1 or 4 wherein the G-protein is a G-protein expressed in a taste receptor cell.

10. The method of claim 9 wherein the G-protein is transducin.

11. The method of claim 10 wherein the effector activation polypeptide comprises the sequence of amino acid residues 293–314 of the transducin alpha-subunit as set forth in FIG. 6 (SEQ ID NO:1).

12. The method of claim 1 or 4 wherein the PDE polypeptide is selected from the group consisting of PDE IA7, PDE IA1, and PDE IC.

13. The method of claim 12 wherein the PDE polypeptide is PDE IA7.

14. The method of claim 12 wherein the PDE polypeptide is PDE IA1.

15. The method of claim 12 wherein the PDE polypeptide is PDE IC.

* * * * *

UNITED STATES PATENT AND TRADEMARK OFFICE
CERTIFICATE OF CORRECTION

PATENT NO.         : 7,179,614 B2
APPLICATION NO.    : 10/380393
DATED              : February 20, 2007
INVENTOR(S)        : Margolskee et al.

It is certified that error appears in the above-identified patent and that said Letters Patent is hereby corrected as shown below:

Col. 1 at lines 13–15, delete "The United States Government may have certain rights to this invention pursuant to these grants." and insert --The government has certain rights in the invention.-- in its place.

Signed and Sealed this

Fifteenth Day of December, 2009

David J. Kappos
*Director of the United States Patent and Trademark Office*

SEQUENCE LISTING

<160> NUMBER OF SEQ ID NOS: 1

<210> SEQ ID NO 1
<211> LENGTH: 350
<212> TYPE: PRT
<213> ORGANISM: Bovine
<220> FEATURE:
<223> OTHER INFORMATION:

<400> SEQUENCE: 1

```
Met Gly Ala Gly Ala Ser Ala Glu Glu Lys His Ser Arg Glu Leu Glu
1               5                   10                  15

Lys Lys Leu Lys Glu Asp Ala Glu Lys Asp Ala Arg Thr Val Lys Leu
            20                  25                  30

Leu Leu Leu Gly Ala Gly Glu Ser Gly Lys Ser Thr Ile Val Lys Gln
        35                  40                  45

Met Lys Ile Ile His Gln Asp Gly Tyr Ser Leu Glu Glu Cys Leu Glu
    50                  55                  60

Phe Ile Ala Ile Ile Tyr Gly Asn Thr Leu Gln Ser Ile Leu Ala Ile
65                  70                  75                  80

Val Arg Ala Met Thr Thr Leu Asn Ile Gln Tyr Gly Asp Ser Ala Arg
                85                  90                  95

Gln Asp Asp Ala Arg Lys Leu Met His Met Ala Asp Thr Ile Glu Glu
            100                 105                 110

Gly Thr Met Pro Lys Glu Met Ser Asp Ile Ile Gln Arg Leu Trp Lys
        115                 120                 125

Asp Ser Gly Ile Gln Ala Cys Phe Asp Arg Ala Ser Glu Tyr Gln Leu
    130                 135                 140

Asn Asp Ser Ala Gly Tyr Tyr Leu Ser Asp Leu Glu Arg Leu Val Thr
145                 150                 155                 160

Pro Gly Tyr Val Pro Thr Glu Gln Asp Val Leu Arg Ser Arg Val Lys
                165                 170                 175

Thr Thr Gly Ile Ile Glu Thr Gln Phe Ser Phe Lys Asp Leu Asn Phe
            180                 185                 190

Arg Met Phe Asp Val Gly Gly Gln Arg Ser Glu Arg Lys Lys Trp Ile
        195                 200                 205

His Cys Phe Glu Gly Val Thr Cys Ile Ile Phe Ile Ala Ala Leu Ser
    210                 215                 220

Ala Tyr Asp Met Val Leu Val Glu Asp Asp Glu Val Asn Arg Met His
225                 230                 235                 240

Glu Ser Leu His Leu Phe Asn Ser Ile Cys Asn His Arg Tyr Phe Ala
                245                 250                 255

Thr Thr Ser Ile Val Leu Phe Leu Asn Lys Lys Asp Val Phe Ser Glu
            260                 265                 270

Lys Ile Lys Lys Ala His Leu Ser Ile Cys Phe Pro Asp Tyr Asn Gly
        275                 280                 285

Pro Asn Thr Tyr Glu Asp Ala Gly Asn Tyr Ile Lys Val Gln Phe Leu
    290                 295                 300

Glu Leu Asn Met Arg Arg Asp Val Lys Glu Ile Tyr Ser His Met Thr
```

-continued

```
             305                 310                 315                 320

Cys Ala Thr Asp Thr Gln Asn Val Lys Phe Val Phe Asp Ala Val Thr
                325                 330                 335

Asp Ile Ile Ile Lys Glu Asn Leu Lys Asp Cys Gly Leu Phe
                340                 345                 350
```